(12) United States Patent
Hayes et al.

(10) Patent No.: US 8,025,680 B2
(45) Date of Patent: Sep. 27, 2011

(54) SYSTEMS AND METHODS FOR POSTERIOR DYNAMIC STABILIZATION OF THE SPINE

(75) Inventors: Stanley Kyle Hayes, Mission Viejo, CA (US); Joey Camia Reglos, Lake Forest, CA (US); Moti Altarac, Irvine, CA (US); Daniel H Kim, Los Altos, CA (US); J Christopher Flaherty, Topsfield, MA (US)

(73) Assignee: Exactech, Inc., Gainesville, FL (US)

( * ) Notice: Subject to any disclaimer, the term of this patent is extended or adjusted under 35 U.S.C. 154(b) by 512 days.

(21) Appl. No.: 11/436,407

(22) Filed: May 17, 2006

(65) Prior Publication Data
US 2008/0097441 A1 Apr. 24, 2008

Related U.S. Application Data

(63) Continuation-in-part of application No. 11/033,452, filed on Jan. 10, 2005, now Pat. No. 7,998,175, which is a continuation-in-part of application No. 11/006,495, filed on Dec. 6, 2004, which is a continuation-in-part of application No. 10/970,366, filed on Oct. 20, 2004.

(51) Int. Cl.
*A61B 17/70* (2006.01)
(52) U.S. Cl. .......... 606/257; 606/258; 606/259
(58) Field of Classification Search ............. 606/246, 606/254–266, 276, 277
See application file for complete search history.

(56) References Cited

U.S. PATENT DOCUMENTS

| 602,580 A | 4/1898 | Haskins et al. |
|---|---|---|
| 802,844 A | 10/1905 | Covell et al. |
| 2,051,248 A | 8/1936 | Dunn |
| 3,807,394 A | 4/1974 | Attenborough |
| 4,611,582 A * | 9/1986 | Duff .................. 606/258 |
| 4,743,260 A | 5/1988 | Burton |
| 5,015,247 A | 5/1991 | Michelson |
| 5,092,866 A | 3/1992 | Breard et al. |
| 5,129,388 A | 7/1992 | Vignaud et al. |
| 5,171,279 A | 12/1992 | Mathews |
| 5,180,393 A | 1/1993 | Commarmond |

(Continued)

FOREIGN PATENT DOCUMENTS
EP 767636 1/1999
(Continued)

OTHER PUBLICATIONS
U.S. Appl. No. 60/701,660.
(Continued)

*Primary Examiner* — Thomas C. Barrett
*Assistant Examiner* — Andrew Yang
(74) *Attorney, Agent, or Firm* — Meyertons, Hood, Kivlin, Kowert & Goetzel, P.C.; Eric B. Meyertons

(57) ABSTRACT

Systems and devices for dynamically stabilizing the spine are provided. The systems include a superior component for attachment to a superior vertebra of a spinal motion segment and an inferior component for attachment to an inferior vertebral of a spinal motion segment. The interconnection between the two components enables the spinal motion segment to move in a manner that mimics the natural motion of the spinal motion segment while substantially offloading the facet joints of the spine. Methods are also provided for stabilizing the spine and for implanting the subject systems.

34 Claims, 24 Drawing Sheets

U.S. PATENT DOCUMENTS

| | | | |
|---|---|---|---|
| 5,282,863 | A | 2/1994 | Burton |
| 5,368,594 | A | 11/1994 | Martin et al. |
| 5,375,823 | A | 12/1994 | Navas |
| 5,387,212 | A * | 2/1995 | Yuan et al. ............ 606/264 |
| 5,415,661 | A | 5/1995 | Holmes |
| 5,437,669 | A | 8/1995 | Yuan et al. |
| 5,437,672 | A * | 8/1995 | Alleyne ............ 606/279 |
| 5,443,467 | A | 8/1995 | Biedermann et al. |
| 5,474,555 | A | 12/1995 | Puno et al. |
| 5,480,401 | A | 1/1996 | Navas |
| 5,484,437 | A | 1/1996 | Michelson |
| 5,489,308 | A | 2/1996 | Kuslich et al. |
| 5,522,843 | A | 6/1996 | Zang |
| 5,527,312 | A | 6/1996 | Ray |
| 5,540,688 | A * | 7/1996 | Navas ............ 606/266 |
| 5,571,191 | A | 11/1996 | Fitz |
| 5,609,636 | A | 3/1997 | Kohrs et al. |
| 5,616,142 | A | 4/1997 | Yuan et al. |
| 5,645,599 | A | 7/1997 | Samani |
| 5,658,337 | A | 8/1997 | Kohrs et al. |
| 5,672,175 | A * | 9/1997 | Martin ............ 606/86 A |
| 5,720,751 | A | 2/1998 | Jackson |
| 5,738,586 | A | 4/1998 | Arriaga |
| 5,741,253 | A | 4/1998 | Michelson |
| 5,776,135 | A | 7/1998 | Errico et al. |
| RE36,211 | E | 5/1999 | Nonomura |
| 5,964,761 | A | 10/1999 | Kambin |
| 6,014,588 | A | 1/2000 | Fitz |
| 6,033,406 | A | 3/2000 | Mathews |
| RE36,758 | E | 6/2000 | Fitz |
| 6,080,155 | A | 6/2000 | Michelson |
| 6,080,157 | A | 6/2000 | Cathro et al. |
| 6,083,224 | A | 7/2000 | Gertzbein et al. |
| 6,096,038 | A | 8/2000 | Michelson |
| 6,132,464 | A | 10/2000 | Martin |
| 6,200,322 | B1 | 3/2001 | Branch et al. |
| 6,241,730 | B1 | 6/2001 | Alby |
| 6,264,656 | B1 | 7/2001 | Michelson |
| 6,267,764 | B1 | 7/2001 | Elberg |
| 6,267,765 | B1 | 7/2001 | Taylor et al. |
| 6,270,498 | B1 | 8/2001 | Michelson |
| 6,273,914 | B1 | 8/2001 | Papas |
| 6,287,764 | B1 | 9/2001 | Hildebrand et al. |
| 6,419,703 | B1 | 7/2002 | Fallin et al. |
| 6,485,518 | B1 | 11/2002 | Cornwall et al. |
| 6,530,929 | B1 | 3/2003 | Justis et al. |
| 6,540,747 | B1 | 4/2003 | Marino |
| 6,547,795 | B2 | 4/2003 | Schneiderman |
| 6,558,390 | B2 | 5/2003 | Cragg |
| 6,562,038 | B1 | 5/2003 | Morrison |
| 6,562,046 | B2 | 5/2003 | Sasso |
| 6,565,605 | B2 | 5/2003 | Goble et al. |
| 6,579,319 | B2 | 6/2003 | Goble et al. |
| 6,610,091 | B1 | 8/2003 | Reiley |
| 6,626,904 | B1 | 9/2003 | Jammet et al. |
| 6,626,905 | B1 | 9/2003 | Schmiel et al. |
| 6,626,944 | B1 | 9/2003 | Taylor |
| 6,645,248 | B2 | 11/2003 | Casutt |
| 6,669,697 | B1 | 12/2003 | Pisharodi |
| 6,669,729 | B2 | 12/2003 | Chin |
| 6,695,842 | B2 | 2/2004 | Zucherman et al. |
| 6,716,245 | B2 | 4/2004 | Pasquet et al. |
| 6,749,613 | B1 | 6/2004 | Conchy et al. |
| 6,749,614 | B2 | 6/2004 | Teitelbaum et al. |
| 6,761,720 | B1 | 7/2004 | Senegas |
| 6,783,527 | B2 | 8/2004 | Drewry et al. |
| 6,802,844 | B2 | 10/2004 | Ferree |
| 6,802,845 | B2 * | 10/2004 | Shirado et al. ............ 606/324 |
| 6,805,697 | B1 | 10/2004 | Helm et al. |
| 6,811,567 | B2 | 11/2004 | Reiley |
| 6,821,277 | B2 | 11/2004 | Teitelbaum |
| 6,835,205 | B2 | 12/2004 | Atkinson et al. |
| 6,835,207 | B2 | 12/2004 | Zacouto et al. |
| 6,875,212 | B2 | 4/2005 | Shaolian et al. |
| 6,899,716 | B2 | 5/2005 | Cragg |
| 6,902,580 | B2 | 6/2005 | Fallin et al. |
| 6,949,123 | B2 | 9/2005 | Reiley |
| 6,966,910 | B2 | 11/2005 | Ritland |
| 6,966,930 | B2 | 11/2005 | Arnin et al. |
| 6,974,478 | B2 | 12/2005 | Reiley et al. |
| 6,986,771 | B2 | 1/2006 | Paul et al. |
| 6,989,011 | B2 | 1/2006 | Paul et al. |
| 6,991,632 | B2 | 1/2006 | Ritland |
| 7,011,660 | B2 | 3/2006 | Sherman et al. |
| 7,011,685 | B2 | 3/2006 | Arnin et al. |
| 7,029,475 | B2 | 4/2006 | Panjabi |
| 7,051,451 | B2 | 5/2006 | Augostino et al. |
| 7,052,497 | B2 | 5/2006 | Sherman et al. |
| 7,056,321 | B2 | 6/2006 | Pagliuca et al. |
| 7,060,068 | B2 | 6/2006 | Tromanhauser et al. |
| 7,066,957 | B2 | 6/2006 | Graf et al. |
| 7,070,598 | B2 | 7/2006 | Lim et al. |
| 7,074,238 | B2 | 7/2006 | Stinson et al. |
| 7,079,883 | B2 | 7/2006 | Marino et al. |
| 7,083,621 | B2 | 8/2006 | Shaolian et al. |
| 7,083,622 | B2 | 8/2006 | Simonson |
| 7,083,649 | B2 | 8/2006 | Zucherman et al. |
| 7,087,055 | B2 | 8/2006 | Lim et al. |
| 7,090,698 | B2 | 8/2006 | Goble et al. |
| 7,108,705 | B2 | 9/2006 | Davison et al. |
| 7,125,410 | B2 | 10/2006 | Freudiger et al. |
| 7,137,985 | B2 | 11/2006 | Jahng |
| 7,182,783 | B2 | 2/2007 | Trieu |
| 7,188,626 | B2 | 3/2007 | Foley et al. |
| 7,207,992 | B2 | 4/2007 | Ritland |
| 7,229,441 | B2 | 6/2007 | Trieu et al. |
| 7,252,673 | B2 | 8/2007 | Lim |
| 7,282,065 | B2 | 10/2007 | Kirschman |
| 7,294,129 | B2 * | 11/2007 | Hawkins et al. ............ 606/86 A |
| 7,306,603 | B2 | 12/2007 | Boehm, Jr. et al. |
| 7,329,258 | B2 | 2/2008 | Studer |
| 7,335,200 | B2 | 2/2008 | Carli et al. |
| 7,341,587 | B2 | 3/2008 | Molz, IV et al. |
| 7,354,453 | B2 | 4/2008 | McAfee |
| 7,361,196 | B2 | 4/2008 | Fallin et al. |
| 7,377,921 | B2 | 5/2008 | Studer et al. |
| 7,377,942 | B2 | 5/2008 | Berry |
| 7,406,775 | B2 | 8/2008 | Funk et al. |
| 7,476,238 | B2 | 1/2009 | Panjabi |
| 7,691,131 | B2 | 4/2010 | Graf |
| 7,776,071 | B2 | 8/2010 | Fortin et al. |
| 7,828,823 | B2 | 11/2010 | Rogeau et al. |
| 7,935,134 | B2 | 5/2011 | Reglos et al. |
| 2001/0037111 | A1 | 11/2001 | Dixon et al. |
| 2002/0065557 | A1 | 5/2002 | Goble et al. |
| 2002/0068975 | A1 | 6/2002 | Teitelbaum et al. |
| 2002/0072800 | A1 | 6/2002 | Goble et al. |
| 2002/0082600 | A1 | 6/2002 | Shaolian et al. |
| 2002/0095154 | A1 | 7/2002 | Atkinson |
| 2002/0120270 | A1 | 8/2002 | Trieu et al. |
| 2002/0123806 | A1 | 9/2002 | Reiley |
| 2002/0133155 | A1 | 9/2002 | Ferree |
| 2002/0151895 | A1 | 10/2002 | Soboleski et al. |
| 2002/0198526 | A1 | 12/2002 | Shaolian et al. |
| 2003/0004572 | A1 | 1/2003 | Goble et al. |
| 2003/0028250 | A1 | 2/2003 | Reiley et al. |
| 2003/0032965 | A1 | 2/2003 | Schneiderman |
| 2003/0040797 | A1 | 2/2003 | Fallin et al. |
| 2003/0055427 | A1 | 3/2003 | Graf |
| 2003/0093078 | A1 | 5/2003 | Ritland |
| 2003/0171749 | A1 | 9/2003 | Le Couedic et al. |
| 2003/0171750 | A1 | 9/2003 | Chin |
| 2003/0208202 | A1 | 11/2003 | Falahee |
| 2003/0208203 | A1 | 11/2003 | Lim et al. |
| 2003/0220642 | A1 | 11/2003 | Freudiger |
| 2003/0220643 | A1 | 11/2003 | Ferree |
| 2003/0229347 | A1 | 12/2003 | Sherman et al. |
| 2003/0236520 | A1 | 12/2003 | Lim et al. |
| 2004/0002708 | A1 | 1/2004 | Ritland |
| 2004/0006341 | A1 | 1/2004 | Shaolian et al. |
| 2004/0006344 | A1 | 1/2004 | Nguyen et al. |
| 2004/0039384 | A1 | 2/2004 | Boehm et al. |
| 2004/0049189 | A1 | 3/2004 | Le Couedic et al. |
| 2004/0064140 | A1 | 4/2004 | Taylor et al. |
| 2004/0073215 | A1 | 4/2004 | Carli |
| 2004/0080418 | A1 | 4/2004 | Dahlborn et al. |
| 2004/0082954 | A1 | 4/2004 | Teitelbaum et al. |

| | | |
|---|---|---|
| 2004/0087947 A1 | 5/2004 | Lim et al. |
| 2004/0092931 A1 | 5/2004 | Taylor et al. |
| 2004/0116927 A1 | 6/2004 | Graf |
| 2004/0127989 A1 | 7/2004 | Dooris et al. |
| 2004/0138662 A1 | 7/2004 | Landry et al. |
| 2004/0143265 A1 | 7/2004 | Landry et al. |
| 2004/0143270 A1 | 7/2004 | Zucherman et al. |
| 2004/0147928 A1 | 7/2004 | Landry et al. |
| 2004/0193158 A1 | 9/2004 | Lim et al. |
| 2004/0215190 A1 | 10/2004 | Nguyen et al. |
| 2004/0225289 A1 | 11/2004 | Biedermann et al. |
| 2004/0230201 A1 | 11/2004 | Yuan et al. |
| 2004/0230304 A1 | 11/2004 | Yuan et al. |
| 2004/0236328 A1* | 11/2004 | Paul et al. .................. 606/61 |
| 2004/0236329 A1 | 11/2004 | Panjabi |
| 2004/0267260 A1 | 12/2004 | Mack et al. |
| 2005/0010217 A1 | 1/2005 | Dalton |
| 2005/0010953 A1 | 1/2005 | Carney et al. |
| 2005/0010954 A1 | 1/2005 | Binder |
| 2005/0010956 A1 | 1/2005 | Moon et al. |
| 2005/0021031 A1 | 1/2005 | Foley et al. |
| 2005/0027361 A1 | 2/2005 | Reiley |
| 2005/0033295 A1 | 2/2005 | Wisnewski |
| 2005/0033434 A1 | 2/2005 | Berry |
| 2005/0033439 A1 | 2/2005 | Gordon et al. |
| 2005/0038432 A1 | 2/2005 | Shaolian et al. |
| 2005/0038440 A1 | 2/2005 | Larson et al. |
| 2005/0043742 A1 | 2/2005 | Bruneau et al. |
| 2005/0043797 A1 | 2/2005 | Lee |
| 2005/0043799 A1 | 2/2005 | Reiley |
| 2005/0049705 A1 | 3/2005 | Hale et al. |
| 2005/0049708 A1 | 3/2005 | Atkinson et al. |
| 2005/0055096 A1 | 3/2005 | Serhan et al. |
| 2005/0056979 A1 | 3/2005 | Studer et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070917 A1 | 3/2005 | Justis |
| 2005/0080418 A1 | 4/2005 | Simonson et al. |
| 2005/0080486 A1 | 4/2005 | Fallin et al. |
| 2005/0085813 A1 | 4/2005 | Spitler et al. |
| 2005/0085815 A1 | 4/2005 | Harms et al. |
| 2005/0085912 A1 | 4/2005 | Arnin et al. |
| 2005/0101953 A1 | 5/2005 | Simonson |
| 2005/0101956 A1 | 5/2005 | Simonson |
| 2005/0102028 A1 | 5/2005 | Arnin et al. |
| 2005/0113927 A1 | 5/2005 | Malek |
| 2005/0119748 A1 | 6/2005 | Reiley et al. |
| 2005/0124991 A1 | 6/2005 | Jahng |
| 2005/0125066 A1 | 6/2005 | McAfee |
| 2005/0131405 A1 | 6/2005 | Molz, IV et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131409 A1 | 6/2005 | Chervitz et al. |
| 2005/0131422 A1 | 6/2005 | Anderson et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0154390 A1 | 7/2005 | Biedermann et al. |
| 2005/0154461 A1 | 7/2005 | Humphreys et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0165396 A1 | 7/2005 | Fortin et al. |
| 2005/0171543 A1* | 8/2005 | Timm et al. .................. 606/61 |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0177240 A1 | 8/2005 | Blain |
| 2005/0182400 A1 | 8/2005 | White |
| 2005/0182401 A1 | 8/2005 | Timm et al. |
| 2005/0182409 A1 | 8/2005 | Callahan et al. |
| 2005/0187548 A1 | 8/2005 | Butler |
| 2005/0192574 A1 | 9/2005 | Blain |
| 2005/0197700 A1 | 9/2005 | Boehm, Jr. et al. |
| 2005/0197705 A1 | 9/2005 | Arnin et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203517 A1 | 9/2005 | Jahng et al. |
| 2005/0209593 A1 | 9/2005 | Kolb |
| 2005/0209694 A1 | 9/2005 | Loeb |
| 2005/0215999 A1 | 9/2005 | Birkmeyer et al. |
| 2005/0216000 A1 | 9/2005 | Colleran et al. |
| 2005/0222569 A1 | 10/2005 | Panjabi |
| 2005/0234551 A1 | 10/2005 | Fallin et al. |
| 2005/0235508 A1 | 10/2005 | Augostino et al. |
| 2005/0240264 A1 | 10/2005 | Tokish, Jr. et al. |
| 2005/0240265 A1 | 10/2005 | Kuiper et al. |
| 2005/0245928 A1 | 11/2005 | Colleran et al. |
| 2005/0245930 A1 | 11/2005 | Timm et al. |
| 2005/0249697 A1 | 11/2005 | Uhrich et al. |
| 2005/0261682 A1 | 11/2005 | Ferree |
| 2005/0261685 A1 | 11/2005 | Fortin et al. |
| 2005/0273167 A1 | 12/2005 | Triplett et al. |
| 2005/0277921 A1 | 12/2005 | Eisermann et al. |
| 2005/0277922 A1 | 12/2005 | Trieu et al. |
| 2005/0288670 A1 | 12/2005 | Panjabi et al. |
| 2006/0015100 A1 | 1/2006 | Panjabi et al. |
| 2006/0036240 A1 | 2/2006 | Colleran et al. |
| 2006/0036244 A1 | 2/2006 | Spitler et al. |
| 2006/0036255 A1 | 2/2006 | Pond et al. |
| 2006/0052785 A1 | 3/2006 | Augostino et al. |
| 2006/0058791 A1 | 3/2006 | Broman et al. |
| 2006/0079894 A1 | 4/2006 | Colleran et al. |
| 2006/0084976 A1 | 4/2006 | Borgstrom et al. |
| 2006/0084982 A1 | 4/2006 | Kim |
| 2006/0084984 A1 | 4/2006 | Kim |
| 2006/0084987 A1 | 4/2006 | Kim |
| 2006/0084991 A1 | 4/2006 | Borgstrom et al. |
| 2006/0085072 A1 | 4/2006 | Funk et al. |
| 2006/0106380 A1 | 5/2006 | Colleran |
| 2006/0106394 A1 | 5/2006 | Colleran |
| 2006/0142759 A1 | 6/2006 | Arnin et al. |
| 2006/0149238 A1 | 7/2006 | Sherman et al. |
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0149375 A1 | 7/2006 | Yuan et al. |
| 2006/0149383 A1 | 7/2006 | Arnin et al. |
| 2006/0149389 A1 | 7/2006 | Romagnoli |
| 2006/0173454 A1 | 8/2006 | Spitler et al. |
| 2006/0189983 A1* | 8/2006 | Fallin et al. .................. 606/61 |
| 2006/0189984 A1 | 8/2006 | Fallin et al. |
| 2006/0190083 A1 | 8/2006 | Arnin et al. |
| 2006/0195086 A1* | 8/2006 | Sybert .................. 606/61 |
| 2006/0195088 A1 | 8/2006 | Sacher et al. |
| 2006/0200137 A1 | 9/2006 | Soboleski |
| 2006/0217718 A1 | 9/2006 | Chervitz et al. |
| 2006/0217719 A1 | 9/2006 | Albert et al. |
| 2006/0235388 A1 | 10/2006 | Justis et al. |
| 2006/0235414 A1 | 10/2006 | Lim et al. |
| 2006/0241642 A1 | 10/2006 | Arnin et al. |
| 2006/0241758 A1 | 10/2006 | Peterman et al. |
| 2006/0241759 A1 | 10/2006 | Trieu |
| 2006/0241768 A1 | 10/2006 | Trieu |
| 2006/0241769 A1 | 10/2006 | Gordon et al. |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247637 A1 | 11/2006 | Colleran et al. |
| 2006/0247650 A1 | 11/2006 | Yerby et al. |
| 2006/0247769 A1 | 11/2006 | Molz et al. |
| 2006/0247773 A1 | 11/2006 | Stamp |
| 2006/0260483 A1 | 11/2006 | Hartmann et al. |

| | | | | | | |
|---|---|---|---|---|---|---|
| 2006/0264934 A1 | 11/2006 | Fallin | | WO | WO-2005070278 | 8/2005 |
| 2006/0264962 A1 | 11/2006 | Chin et al. | | WO | WO-2005070349 | 8/2005 |
| 2006/0265074 A1* | 11/2006 | Krishna et al. ............ 623/17.15 | | WO | WO-2005070350 | 8/2005 |
| 2006/0271198 A1 | 11/2006 | McAfee | | WO | WO-2005070351 | 8/2005 |
| 2006/0276801 A1 | 12/2006 | Yerby et al. | | WO | WO-2005070352 | 8/2005 |
| 2006/0276897 A1 | 12/2006 | Winslow et al. | | WO | WO-2005070353 | 8/2005 |
| 2006/0282075 A1 | 12/2006 | Labrom et al. | | WO | WO-2005070354 | 8/2005 |
| 2006/0282077 A1 | 12/2006 | Labrom et al. | | WO | WO-2005077113 | 8/2005 |
| 2006/0282078 A1 | 12/2006 | Labrom et al. | | WO | WO-2005079426 | 9/2005 |
| 2006/0282079 A1 | 12/2006 | Labrom et al. | | WO | WO-2005079672 | 9/2005 |
| 2006/0282080 A1 | 12/2006 | Albert et al. | | WO | WO-2005079711 | 9/2005 |
| 2006/0293657 A1 | 12/2006 | Hartmann | | WO | WO-2005084590 | 9/2005 |
| 2007/0005062 A1 | 1/2007 | Lange et al. | | WO | WO-2005087121 | 9/2005 |
| 2007/0005063 A1 | 1/2007 | Bruneau et al. | | WO | WO-2005092223 | 10/2005 |
| 2007/0016191 A1 | 1/2007 | Culbert et al. | | WO | WO-2005094704 | 10/2005 |
| 2007/0016193 A1 | 1/2007 | Ritland | | WO | WO-2006016371 | 2/2006 |
| 2007/0016195 A1 | 1/2007 | Winslow et al. | | WO | WO-2006017507 | 2/2006 |
| 2007/0016196 A1 | 1/2007 | Winslow et al. | | WO | 2006045091 | 4/2006 |
| 2007/0016218 A1 | 1/2007 | Winslow et al. | | WO | WO-2006042188 | 4/2006 |
| 2007/0016296 A1 | 1/2007 | Triplett et al. | | WO | WO-2006042189 | 4/2006 |
| 2007/0043358 A1 | 2/2007 | Molz et al. | | WO | WO-2006047363 | 5/2006 |
| 2007/0043359 A1 | 2/2007 | Altarac | | WO | WO-2006063107 | 6/2006 |
| 2007/0049931 A1 | 3/2007 | Justis et al. | | WO | WO-2006102443 | 9/2006 |
| 2007/0055257 A1 | 3/2007 | Vaccaro et al. | | WO | WO-2006108067 | 10/2006 |
| 2007/0073289 A1* | 3/2007 | Kwak et al. ..................... 606/61 | | WO | WO-2006125142 | 11/2006 |
| 2007/0100341 A1 | 5/2007 | Reglos et al. | | WO | 2007014119 | 2/2007 |
| 2007/0118122 A1 | 5/2007 | Butler et al. | | WO | WO-2007021588 | 2/2007 |
| 2007/0161988 A1 | 7/2007 | Drewry et al. | | WO | WO-2007075375 | 7/2007 |
| 2007/0161997 A1 | 7/2007 | Thramann et al. | | WO | 2007117366 | 10/2007 |
| 2007/0239159 A1 | 10/2007 | Altarac et al. | | WO | 2007136612 | 11/2007 |
| 2008/0045951 A1 | 2/2008 | Fanger et al. | | WO | 2008069835 | 6/2008 |
| 2008/0097441 A1 | 4/2008 | Hayes et al. | | WO | 2008153747 | 12/2008 |
| 2008/0154307 A1 | 6/2008 | Colleran et al. | | WO | 2009042489 | 4/2009 |
| 2008/0262554 A1 | 10/2008 | Reglos et al. | | WO | 2009100190 | 8/2009 |
| 2009/0030465 A1 | 1/2009 | Altarac et al. | | WO | 2010019791 | 2/2010 |
| 2009/0228045 A1 | 9/2009 | Hayes et al. | | | | |
| 2010/0036423 A1 | 2/2010 | Hayes et al. | | | | |

FOREIGN PATENT DOCUMENTS

| | | |
|---|---|---|
| EP | 0951246 | 10/1999 |
| EP | 0986339 | 3/2000 |
| EP | 1056408 | 12/2000 |
| EP | 1138268 | 10/2001 |
| EP | 1145602 | 10/2001 |
| EP | 1303225 | 4/2003 |
| EP | 1399078 | 3/2004 |
| EP | 1415602 | 5/2004 |
| EP | 1415603 | 7/2005 |
| EP | 1810624 | 7/2007 |
| FR | 2728454 | 6/1996 |
| WO | WO-9116018 | 10/1991 |
| WO | WO-9426192 | 11/1994 |
| WO | WO-9600049 | 1/1996 |
| WO | WO-9848717 | 11/1998 |
| WO | WO-9855038 | 12/1998 |
| WO | WO-0062684 | 10/2000 |
| WO | WO-0130248 | 5/2001 |
| WO | WO-0141681 | 6/2001 |
| WO | WO-0238060 | 5/2002 |
| WO | WO-02065954 | 8/2002 |
| WO | WO-02067793 | 9/2002 |
| WO | WO-02102259 | 12/2002 |
| WO | WO-03047442 | 6/2003 |
| WO | WO-03075805 | 9/2003 |
| WO | WO-03094699 | 11/2003 |
| WO | WO-03101350 | 12/2003 |
| WO | WO-2004008949 A3 | 1/2004 |
| WO | WO-2004047617 A3 | 6/2004 |
| WO | WO-2005030029 | 4/2005 |
| WO | WO-2005030031 | 4/2005 |
| WO | WO-2005030066 | 4/2005 |
| WO | WO-2005030067 | 4/2005 |
| WO | WO-2005041799 | 5/2005 |
| WO | WO-2005044152 | 5/2005 |
| WO | WO-2005046515 | 5/2005 |
| WO | WO-2005053572 | 6/2005 |
| WO | WO-2005055874 | 6/2005 |
| WO | 2005065516 | 7/2005 |
| WO | WO-2005067824 | 7/2005 |

OTHER PUBLICATIONS

Non-Final Office Action for U.S. Appl. No. 11/006,495, Mail Date Jun. 30, 2008, 27 pages.
International Search Report and Written Opinion for application No. PCT/US06/28586, Mail Date Jul. 27, 2007, 14 pages.
International Search Report and Written Opinion for application No. PCT/US07/04726, Mail Date Jul. 8, 2008, 7 pages.
International Search Report and Written Opinion for application No. PCT/US05/38021, Mail Date Apr. 10, 2006, 7 pages.
International Search Report and Written Opinion for application No. PCT/US07/11573, Mail Date Apr. 23, 2008, 8 pages.
Final Office Action for U.S. Appl. No. 10/970,366, Mail Date: Oct. 5, 2009, 8 pages.
Non-Final Office Action for U.S. Appl. No. 10/970,366, Mail Date: Nov. 25, 2008, 7 pages.
Non-Final Office Action for U.S. Appl. No. 11/006,495, Mail Date: Jun. 30, 2008, 9 pages.
Final Office Action for U.S. Appl. No. 11/006,495, Mail Date: Mar. 20, 2009, 8 pages.
Non-Final Office Action for U.S. Appl. No. 11/006,495, Mail Date: Dec. 29, 2009, 9 pages.
Non-Final Office Action for U.S. Appl. No. 11/033,452, Mail Date: Dec. 11, 2008, 6 pages.
Non-Final Office Action for U.S. Appl. No. 11/033,452, Mail Date: Oct. 13, 2009, 7 pages.
Non-Final Office Action for U.S. Appl. No. 11/427,738, Mail Date: Dec. 29, 2009, pp. 8.
Non-Final Office Action for U.S. Appl. No. 11/362,366, Mail Date: Apr. 7, 2009, pp. 6.
Final Office Action for U.S. Appl. No. 10/970,366, mailed Jan. 13, 2011.
Advisory Action for U.S. Appl. No. 11/006,495, mailed Dec. 30, 2010.
Non-Final Office Action for U.S. Appl. No. 11/033,452, mailed Dec. 23, 2010.
Non-Final Office Action for U.S. Appl. No. 11/362,366 mailed Mar. 18, 2011.
International Search Report for application No. PCT/US07/11597, Applicant: Vertiflex, Inc.; Mail Date Oct. 2, 2008, 2 pages.

International Preliminary Report on Patentability (mailed on Nov. 17, 2008) and Written Opinion (mailed on Oct. 2, 2008) for application No. PCT/US07/11597, Applicant: Vertiflex, Inc.; 6 pages.
Non-Final Office Action for U.S. Appl. No. 11/427,738, mailed Mar. 10, 2009.
Non-Final Office Action for U.S. Appl. No. 11/427,738, mailed Aug. 5, 2010.
International Search Report (mailed on Apr. 23, 2008) for application No. PCT/US07/11573, pp. 1.
International Preliminary Report on Patentability (issued on Nov. 17, 2008) and Written Opinion (mailed on Apr. 23, 2008) for application No. PCT/US07/11573, pp. 4.
International Search Report (mailed on Jul. 27, 2007) for application No. PCT/US06/28586, pp. 2
International Preliminary Report on Patentability (issued on Jan. 22, 2008) and Written Opinion (mailed on Jul. 27, 2007) for application No. PCT/US06/28586, pp. 9.
International Search Report (mailed on Dec. 19, 2008) for Application No. PCT/US2008/006598, pp. 2.
International Preliminary Report on Patentability (mailed on Dec. 1, 2009) and Written Opinion (mailed on Dec. 19, 2008) for Application No. PCT/US2008/006598, pp. 5.
International Search Report (mailed on Mar. 31, 2009) for Application No. PCT/US2008/076815, pp. 3.
International Preliminary Report on Patentability (mailed on Mar. 24, 2010) and Written Opinion (mailed on Mar. 31, 2009) for Application No. PCT/US2008/076815, pp. 5.
International Search Report for application No. PCT/US09/033174, Mail Date Aug. 27, 2009, 2 pages.
International Preliminary Report on Patentability (issued on Aug. 10, 2010) and Written Opinion (mailed on Aug. 27, 2009) for application No. PCT/US09/033174, 5 pages.
International Search Report and Written Opinion for application No. PCT/US09/053740, Mail Date Mar. 24, 2010, 4 pages.
International Preliminary Report on Patentability and Written Opinion for application No. PCT/US09/053740, Mail Date Mar. 24, 2010, 11 pages.
International Preliminary Report on Patentability (issued on Aug. 26, 2008) and Written Opinion (mailed on Jul. 8, 2008) for application No. PCT/US07/04726, 4 pages.
International Search Report (mailed on Jul. 8, 2008) for application No. PCT/US07/04726, pp. 1.
Requirement for Restriction/Election for U.S. Appl. No. 10/970,366, mailed Apr. 3, 2008.
Non-Final Office Action for U.S. Appl. No. 10/970,366, mailed Aug. 5, 2010.
Final Office Action for U.S. Appl. No. 11/006,495, mailed Sep. 16, 2010.
Final Office Action for U.S. Appl. No. 11/033,452, mailed Aug. 5, 2010.
International Search Report (mailed on Apr. 10, 2006) for application No. PCT/US05/38021, pp. 1.
International Preliminary Report on Patentability (issued on Apr. 24, 2007) and Written Opinion (mailed on Apr. 10, 2008) for application No. PCT/US05/38021, pp. 4.
Examiner's First Report on Australian Patent Application No. 2005295209 mailed on Jun. 22, 2010, pp. 3.
European Supplementary Search Report for Application No. EP05816030; Applicant: Vertiflex, Inc.; Date Mail: Sep. 7, 2009, pp. 6.
Final Office Action for U.S. Appl. No. 11/362,366, mailed Apr. 23, 2010, pp. 6.
Non-Final Office Action for U.S. Appl. No. 12/154,540 mailed on Apr. 11, 2011.
Non-Final Office Action for U.S. Appl. No. 12/233,212 mailed on Apr. 5, 2011.
Non-Final Office Action for U.S. Appl. No. 12/366,089 mailed on Apr. 12, 2011.
Advisory Action for U.S. Appl. No. 10/970,366 mailed on Apr. 28, 2011.
Non-Final Office Action for U.S. Appl. No. 11/006,495 mailed on Mar. 31, 2011.
Communication pursuant to Article 94(3) EPC for Application No. EP05816030; Applicant: Vertiflex, Inc.; Date Mail: May 2, 2011, pp. 9.

* cited by examiner

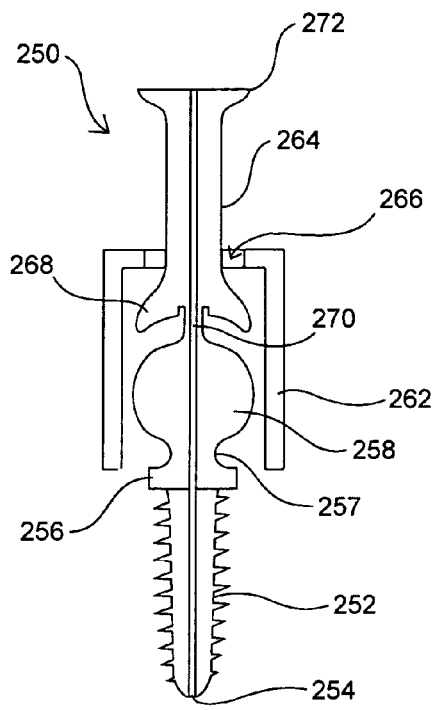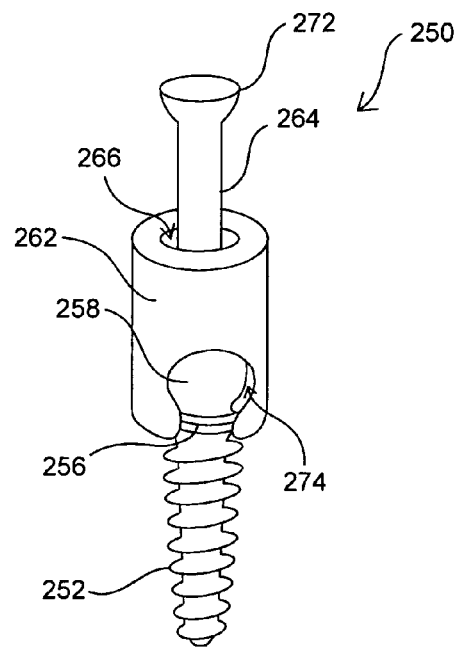
FIG. 14A  FIG. 14B
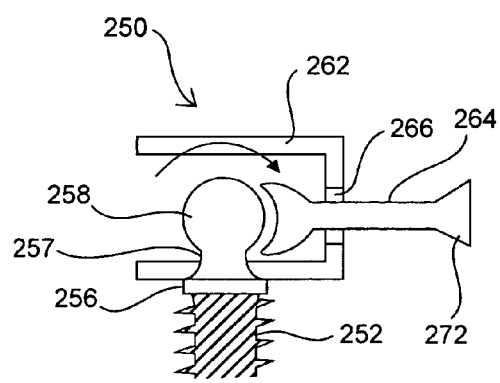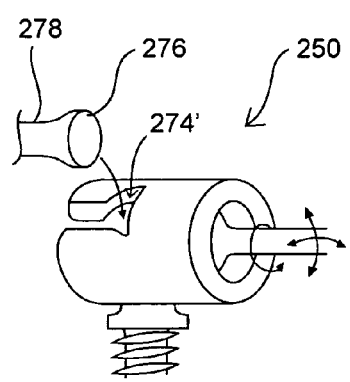
FIG. 14C  FIG. 14D

SYSTEMS AND METHODS FOR POSTERIOR DYNAMIC STABILIZATION OF THE SPINE

CROSS-REFERENCE TO RELATED APPLICATIONS

This application is a continuation-in-part of U.S. patent application Ser. No. 11/033,452, filed on Jan. 10, 2005, which is a continuation-in-part of U.S. patent application Ser. No. 11/006,495, filed on Dec. 6, 2004, which is a continuation-in-part application of U.S. Ser. No. 10/970,366, filed Oct. 20, 2004, incorporated herein by reference.

FIELD OF THE INVENTION

The present invention is directed towards the treatment of spinal disorders and pain. More particularly, the present invention is directed to systems and methods of treating the spine, which eliminate pain and enable spinal motion, which effectively mimic that of a normally functioning spine.

BACKGROUND OF THE INVENTION

FIGS. 1A and 1B illustrate a portion of the human spine having a superior vertebra 2 and an inferior vertebra 4, with an intervertebral disc 6 located in between the two vertebral bodies. The superior vertebra 2 has superior facet joints 8a and 8b, inferior facet joints 10a and 10b, posterior arch 16 and spinous process 18. Pedicles 3a and 3b interconnect the respective superior facet joints 8a, 8b to the vertebral body 2. Extending laterally from superior facet joints 8a, 8b are transverse processes 7a and 7b, respectively.

Extending between each inferior facet joint 10a and 10b and the spinous process 18 are lamina 5a and 5b, respectively. Similarly, inferior vertebra 4 has superior facet joints 12a and 12b, superior pedicles 9a and 9b, transverse processes 11a and 11b, inferior facet joints 14a and 14b, lamina 15a and 15b, posterior arch 20, spinous process 22.

The superior vertebra with its inferior facets, the inferior vertebra with its superior facets, the intervertebral disc, and seven spinal ligaments (not shown) extending between the superior and inferior vertebrae together comprise a spinal motion segment or functional spine unit. Each spinal motion segment enables motion along three orthogonal axes, both in rotation and in translation. The various spinal motions are illustrated in FIGS. 1C-1E. In particular, FIG. 1C illustrates flexion and extension motions and axial loading, FIG. 1D illustrates lateral bending motion and translation, and FIG. 1E illustrates axial rotational motion. A normally functioning spinal motion segment provides physiological limits and stiffness in each rotational and translational direction to create a stable and strong column structure to support physiological loads.

Traumatic, inflammatory, metabolic, synovial, neoplastic and degenerative disorders of the spine can produce debilitating pain that can affect a spinal motion segment's ability to properly function. The specific location or source of spinal pain is most often an affected intervertebral disc or facet joint, and in particular the nerves in and around the intervertebral disc or facet joint. Often, a disorder in one location or spinal component can lead to eventual deterioration or disorder, and ultimately, pain in another.

Spine fusion (arthrodesis) is a procedure in which two or more adjacent vertebral bodies are fused together once the natural height of the degenerated disc has been restored. It is one of the most common approaches to alleviating various types of spinal pain, particularly pain associated with one or more affected intervertebral discs. However, fusion is only as good as the ability to restore disc height to relieve the pain by taking pressure off the nerves, nerve roots, and/or articulating surfaces—i.e., facet joints and end plates of the vertebral bodies. While spine fusion generally helps to eliminate certain types of pain, it has been shown to decrease function by limiting the range of motion for patients in flexion, extension, rotation and lateral bending. Furthermore, fusion creates increased stresses on adjacent non-fused motion segments and accelerated degeneration of the motion segments. Additionally, pseudarthrosis (resulting from an incomplete or ineffective fusion) may not provide stability of the degenerative spine or the expected pain-relief for the patient. Also, the device(s) used for fusion, whether artificial or biological, may migrate out of the fusion site creating significant new problems for the patient. In addition, fusion of the spine causes the increased transfer of stresses to the anatomical structures above and below the site of fusion. The additional stresses may cause the accelerated degeneration of anatomical structures above and below the original site of fixation, thus necessitating further surgical intervention in order to arrest the degeneration of these levels, to restore stability of the degenerated spine, and to relieve the pain associated with this process.

Various technologies and approaches have been developed to treat spinal pain without fusion in order to maintain or recreate the natural biomechanics of the spine. To this end, significant efforts are being made in the use of implantable artificial intervertebral discs. Artificial discs are intended to replace the natural disc while restoring articulation between vertebral bodies so as to recreate the full range of motion normally allowed by the elastic properties of the natural disc. Unfortunately, the currently available artificial discs do not adequately address all of the mechanics of motion for the spinal column.

It has been found that the facet joints can also be a significant source of spinal disorders and debilitating pain. For example, a patient may suffer from arthritic facet joints, severe facet joint tropism, otherwise deformed facet joints, facet joint injuries, etc. These disorders lead to spinal stenosis, degenerative spondylolithesis, and/or isthmic spondylotlisthesis, pinching the nerves which extend or exit the foramen, i.e., the space between the intervetebral bodies, and between the affected vertebrae.

Current interventions for the treatment of facet joint disorders have not been found to provide completely successful results. One reason may be that facet disorders and degenerative disease are usually preceded by degenerative problems associated with the disc that may result in stensosis, etc. As the disc degenerates, the height of the vertebral disc starts to collapse which increases the stresses on the facet joint, which in turn causes degeneration of the facet joint. Degeneration of the structures in the spine leads to increased stresses on the structures. As a natural response the body attempts to build bone that typically leads to stenosis of the spinal canal or the foramen. Facetectomy (removal of the facet joints) may provide some pain relief, but as the facet joints help to support axial, torsional, and shear loads (approximately 20% of the total load) that act on the spinal column in addition to providing a sliding articulation and mechanism for load transmission, their removal may undesiredly allow hypermobility of the spine. Laminectomy (removal of the lamina, including the spinal arch and the spinous process) may also provide pain relief associated with facet joint disorders; however, the spine is made less stable and is subject to hypermobility. Problems with the facet joints can also complicate treatments associated with other portions of the spine. In fact, contraindications for disc replacement include arthritic facet joints, absent facet joints, severe facet joint tropism, or otherwise deformed facet joints due to the inability of the artificial disc (when used with compromised or missing facet joints) to properly restore the natural height of the disc while allowing natural biomechanics of the spinal motion segment.

While various attempts have been made at facet joint replacement, they have been inadequate. This is due to the fact that prosthetic facet joints preserve existing bony structures and therefore do not address pathologies which affect facet joints themselves. Certain facet joint prostheses, such as those disclosed in U.S. Pat. No. 6,132,464, are intended to be supported on the lamina or the posterior arch. As the lamina is a very complex and highly variable anatomical structure, it is very difficult to design a prosthesis that provides reproducible positioning against the lamina to correctly locate the prosthetic facet joints. In addition, when facet joint replacement involves complete removal and replacement of the natural facetjoint, as disclosed in U.S. Pat. No. 6,579,319, the prosthesis is unlikely to endure the loads and cycling experienced by the vertebra. Thus, the facet joint replacement may be subject to long-term displacement. Furthermore, when facet joint disorders are accompanied by disease or trauma to other structures of a vertebra (such as the lamina, spinous process, and/or transverse processes), facet joint replacement is insufficient to treat the problem(s).

Most recently, surgical-based technologies, referred to as "dynamic posterior stabilization," have been developed to address spinal pain resulting from more than one disorder, when more than one structure of the spine have been compromised. An objective of such technologies is to provide the support of fusion-based implants while maximizing the natural biomechanics of the spine. This approach helps reduce the amount of stress transmitted or shifted to the level above or below that which is being treated to reduce the acceleration of the degenerative process typically seen in rigid devices used to fuse the spine. Dynamic posterior stabilization systems typically fall into one of two general categories: (1) interspinous spacers and (2) posterior pedicle screw-based systems.

Examples of interspinous spacers are disclosed in U.S. Pat. Nos. Re. 36,211, 5,645,599, 6,695,842, 6,716,245 and 6,761,720. The spacers, which are made of either a hard or compliant material, are placed between adjacent spinous processes. Because the interspinous spacers involve attachment to the spinous processes, use of these types of systems is limited to applications where the spinous processes are uncompromised and healthy.

Examples of pedicle screw-based systems are disclosed in U.S. Pat. Nos. 5,015,247, 5,484,437, 5,489,308, 5,609,636 and 5,658,337, 5,741,253, 6,080,155, 6,096,038, 6,264,656 and 6,270,498. These types of systems involve the use of screws which are positioned in the vertebral body through the pedicle. Certain types of these pedicle screw-based systems may be used to augment compromised facet joints, while others require removal of the spinous process and/or the facet joints for implantation. One such system, the Zimmer Spine Dynesys® employs a cord which is extended between the pedicle screws and a fairly rigid spacer which is passed over the cord and positioned between the screws. While this system is able to provide load sharing and restoration of disc height, because it is so rigid, it is not effective in preserving the natural motion of the spinal segment into which it is implanted. Other pedicle screw-based systems employ articulating joints between the vertebral bodies which are intended to replace the facet joints, and are anchored to the veterbral bodies via the pedicle screws.

With the limitations of current spine stabilization technologies, there is clearly a need for an improved means and method for dynamic posterior stabilization of the spine which address the drawbacks of prior devices. In particular, it would be highly beneficial to have a dynamic stabilization system that enables the spine to mimic the motion of one or more healthy and uncompromised vertebral segments without limiting natural extension/flexion, axial rotational and lateral bending movements. It would be additionally beneficial if such a system could be used to treat all spinal indications regardless of pain source, prevent or slow the deterioration of the intervertebral discs, or even restore disc height, and be used in conjunction with prosthetic intervertebral discs.

SUMMARY OF THE INVENTION

The present invention provides methods, systems and devices for dynamically stabilizing the spine. The systems include a superior component for attachment to a superior vertebra of a spinal motion segment and an inferior component for attachment to an inferior vertebra of a spinal motion segment. The interconnection between the two components enables the spinal motion segment to move in a manner that mimics the natural motion of the spinal motion segment. In various embodiments, the superior and/or inferior components are connected by one or more strut members which interface or adjustably interconnect between the two components. In certain embodiments, the strut or struts include at least one joint which may be compressible and/or distractable. In other embodiments, the length, stiffness or shape of the strut may be adjustable. The systems may be configured to include additional components for the treatment of more than one spinal segment. Moreover, certain of the implementation methods may be configured for implantation without the removal of any portion of the spinal motion segment.

The present invention also includes methods for stabilizing at least one spinal motion segment where the methods involve implantation of the subject systems. attaching the components to the vertebrae.

Certain embodiments of the invention provide a sustaining force to distract the facets to offload the joint which reduces or eliminates facet pain, while allowing maximum mobility of the natural movement of the spine. Targeted and predetermined limitations to mobility may also be provided. The load may be shared with an existing facet or the load may be fully supported by devices according to the invention, which may include axial, torsional, and shearing loads. Devices according to the invention may provide stiffness, e.g., resistance to motion or hypermobility, to limit previous physiological stiffness, e.g., after bone removal, or to further resist motion from current stiffness, e.g., to prevent pain.

Advantages of certain embodiments of the invention may include one or more of the following. The natural biomechanics and motion of the spine are maintained to a greater degree than in prior systems, including fusion. Load on the facet joints may be offloaded. Spinal motion is preserved, including at least four degrees of freedom including forward flexion and extension, axial rotation, lateral bending and translation. Devices according to the invention may have a low profile and be minimally invasive and they may be conveniently delivered through a cannula. In other words, devices according to embodiments of the invention may be delivered in a minimally invasive way, or in a "mini-open" procedure, or in an open procedure, or all three. The degrees of freedom of certain embodiments of the invention are such that accidental loosening of the pedicle screws over time in use is minimized over that encountered in prior systems.

Systems according to the invention may be employed to treat various spinal disorders and pain, including those involving arthritic facet joints, severe facet joint tropism, facet joint injuries, deformed facetjoints, scoliosis, etc.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 8A shows the pivoting rod assembly and FIG. 8B shows a receiving assembly.

FIGS. 14A-14D illustrate various views of a breakaway pedicle screw head design that may be employed in the dynamic stabilization system of the present invention.

DETAILED DESCRIPTION OF THE INVENTION

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise.

Thus, for example, reference to "a spinal segment" may include a plurality of such spinal segments and reference to "the screw" includes reference to one or more screws and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention.

The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1A:
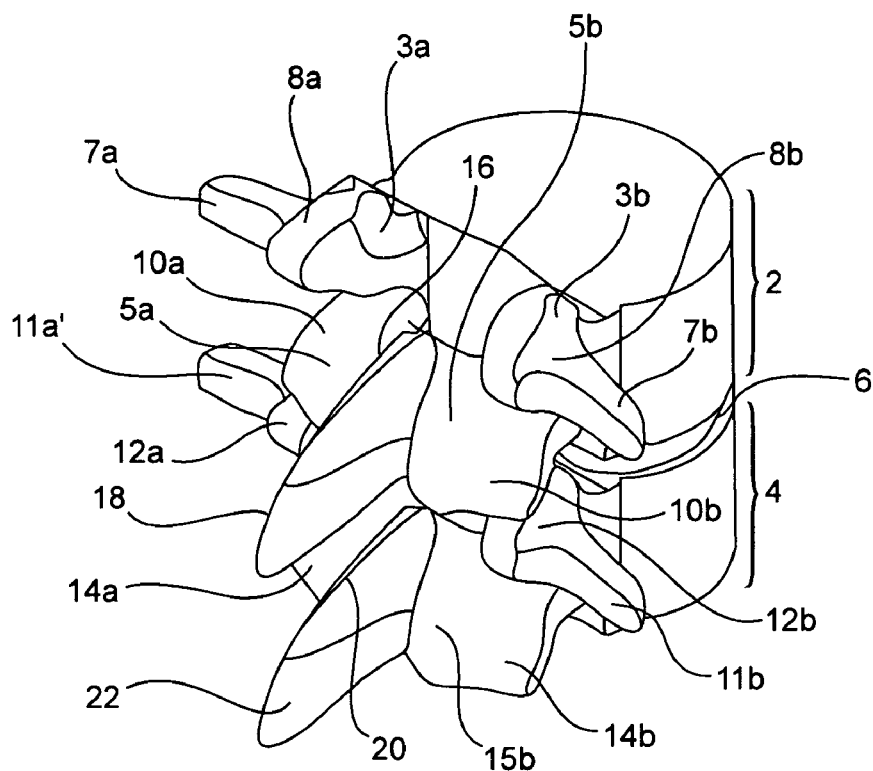
FIGS. 1A and 1B illustrate perspective views of a portion of the human spine having two vertebral segments, where the spinous process and the lamina of the superior vertebra have been resected in FIG. 1B.

The present invention will now be described in greater detail by way of the following description of exemplary embodiments and variations of the systems and methods of the present invention. While more fully described in the context of the description of the subject methods of implanting the subject systems, it should be initially noted that in certain applications where the natural facet joints are compromised, as illustrated in FIG. 1A, inferior facets 10a and 10b, lamina 5a and 5b, posterior arch 16 and spinous process 18 of superior vertebra 2 may be resected for purposes of implantation of certain of the dynamic stabilization systems of the present invention. In other applications, where possible, the natural facet joints, lamina and/or spinous are spared and left intact for implantation of other dynamic stabilization systems of the present invention.

It should also be understood that the term "system", when referring to a system of the present invention, most typically refers to a set of components which includes a superior, cephalad or rostral (towards the head) component configured for implantation into a superior vertebra of a vertebral motion segment and an inferior or caudal (towards the feet) component configured for implantation into an inferior vertebra of a vertebral motion segment. A pair of such component sets includes one set of components configured for implantation into and stabilization of the left side of a vertebral segment and another set configured for the implantation into and stabilization of the right side of a vertebral segment. The left set of components may move independently of the right set of components or their motions may be coordinated via an attachment between the two. In other words, they may move in conjunction with one another, with both moving relative to the more fixed attachment between the two. Where multiple spinal segments or units are being treated, the term "system" may refer to two or more pairs of component sets, i.e., two or more left sets and/or two or more right sets of components. Such a multilevel system involves stacking of component sets in which each set includes a superior component, an inferior component, and one or more medial components therebetween. These multilevel systems may include cross member components or strut systems having differing properties, e.g., lengths, limits on travel or other limited range of motion; resistance to motion or other forces, attachment locations, etc.

The superior and inferior components (and any medial components therebetween), when operatively implanted, are engaged or interface with each other in a manner that enables the treated spinal motion segment to mimic the function and movement of a natural healthy segment. The interconnecting strut system, or interface means, includes one or more structures or members which enable, limit and/or otherwise selectively control spinal motion. The structures may perform such functions by exerting various forces on the system components, and thus on the target vertebrae. The manner of coupling, interfacing, engagement or interconnection between the subject system components may involve compression, distraction, rotation or torsion, or a combination thereof. In certain embodiments, the extent or degree of these forces or motions between the components may be intraoperatively selected and/or adjusted to address the condition being treated, to accommodate the particular spinal anatomy into which the system is implanted, and to achieve the desired therapeutic result, such as to restore disc height and offset the facet joints.

In certain embodiments, the superior and inferior components are mechanically coupled to each other by one or more interconnection or interfacing means. In other embodiments, the superior and inferior components interface in an engaging manner which does not necessarily mechanically couple or fix the components together but rather constrains their relative movement and also enables the treated spinal motion segment to mimic the natural function and movement of a healthy segment. Typically, the interconnecting means is a posteriorly positioned component, i.e., one positioned posteriorly of the superior and inferior components, or it may be a laterally positioned component, i.e., one positioned to the outer side of the posterior and inferior components. The structures may involve one or more strut systems and/or joints which provide for dynamic movement of a stabilized spinal motion segment.

Figure 1B:
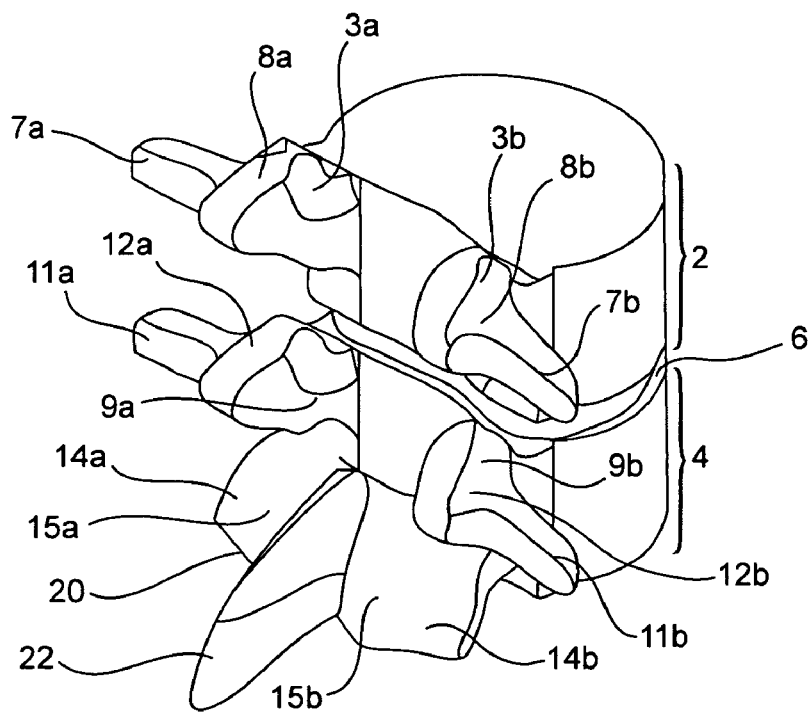
Figure 1C:
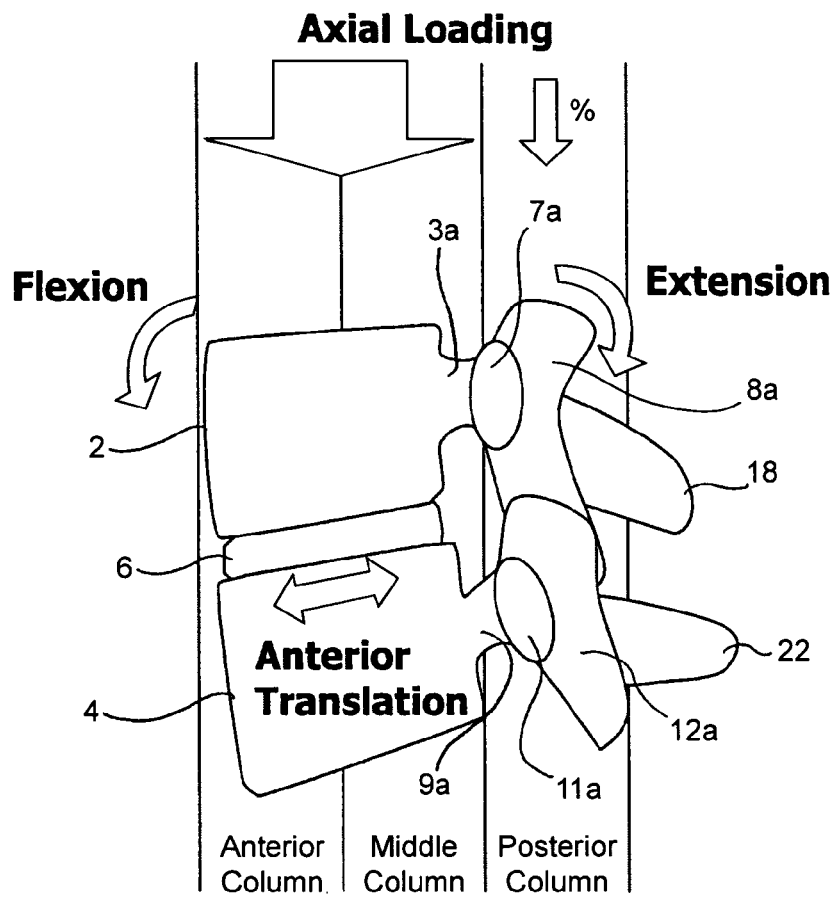
FIGS. 1C, 1D and 1E illustrate sagittal, anterior-posterior (A-P), and cephalad-caudal views, respectively, of the spinal segments of FIGS. 1A and 1B under going various motion.
Figure 1D:
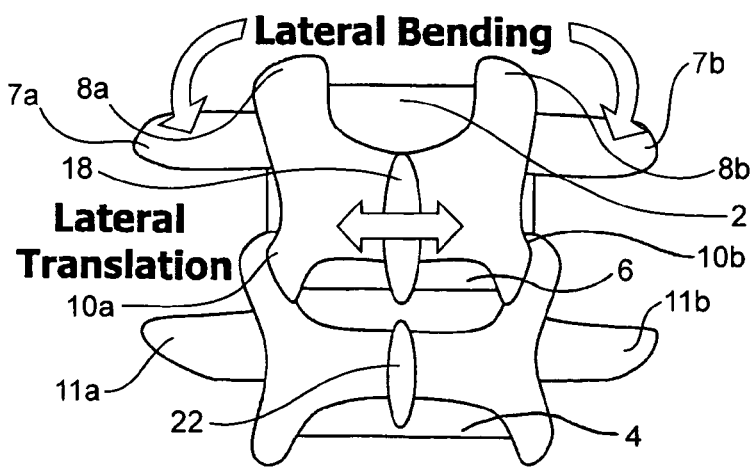
Figure 1E:
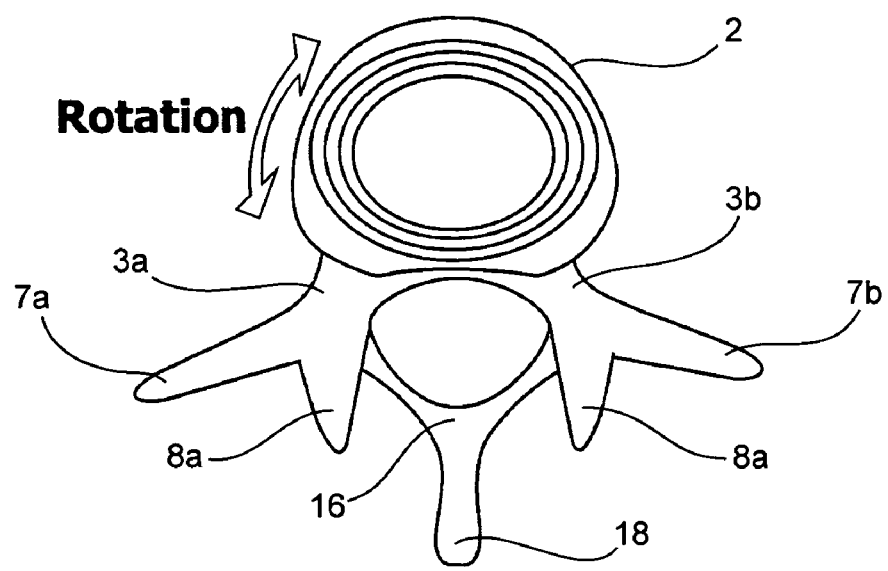
Figure 2:
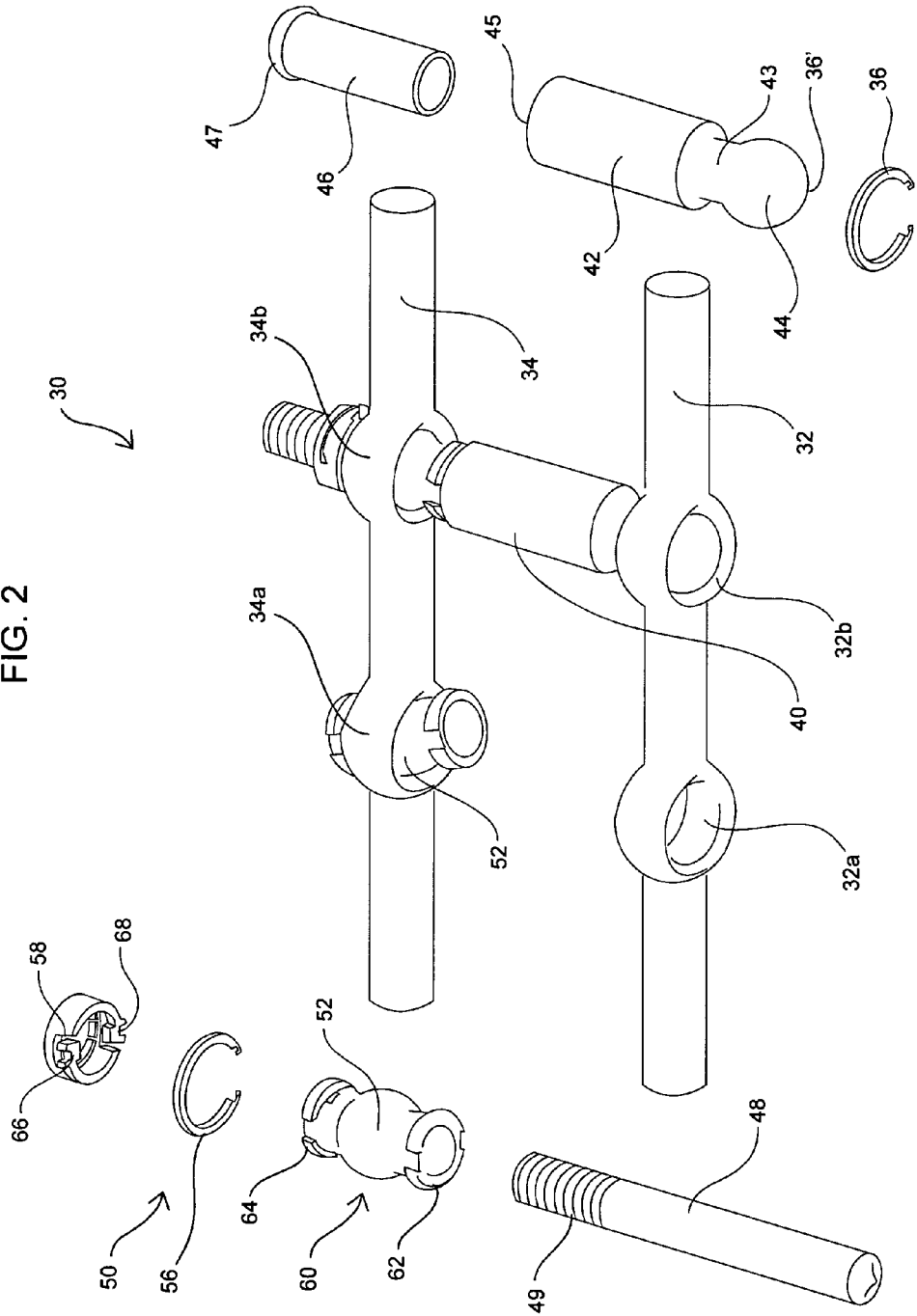
FIG. 2 illustrates a perspective exploded view of an embodiment of a dynamic stabilization system of the present invention.

Referring now to FIG. 2, there is illustrated a dynamic stabilization system 30 which may be operatively implanted into the vertebral segment of FIGS. 1A and 1B. The system 30 may be made, e.g., of titanium or a titanium alloy, stainless steel, and/or one or more polymers, and may be implanted or clamped onto generally two adjacent spinal segments to stabilize one with respect to the other.

Of course it should be noted that the system may be applied to multi-level segments as well, and various embodiments of this are disclosed below. In some cases, however, it may be undesired or contraindicated to install a pedicle screw in a particular vertebral segment, e.g., the segment may be too diseased for a pedicle screw installation. In this case, one segment of a multilevel system may be skipped, with the segments adjacent to the skipped segment being used to secure the pedicle screw systems. In this case, the strut systems employed may be, e.g., twice as long as for a single segment facet augmentation.

The system 30 includes a superior pedicular cross member component 34 and an inferior pedicular cross member component 32. The lengths of superior pedicular cross member component 34 and inferior pedicular cross member component 32 are generally chosen to accommodate the geometry of a patient's vertebrae and also to accommodate various pedicle screw systems which may affix the cross member components and accompanying systems to the spine. The pedicular cross member components may be chosen to fit closely between the spinous processes, such that removal of parts of the spinous processes is unnecessary. The pedicular cross member components may also be made very small in extent, such that they provide a platform for, e.g., attaching a component, but do not even extend over to another pedicle screw.

The superior pedicular cross member component 34 is connected to the inferior pedicular cross member component 32 by a strut system 40, only one of which is shown in FIG. 2. Note that for clarity no pedicle screws or clamps are shown in FIG. 2. Typically two strut systems are appropriate, one on each side of the spinous process. The length of strut system 40 is chosen generally by the geometry of the patient's spine as well as the range of motion desired. The pedicular cross member components generally have a number of voids formed therein, shown in the figure as two voids, for partially enclosing and capturing the strut systems, shown in FIG. 2 as voids 34a and 34b within superior pedicular cross member component 34 and voids 32a and 32b within inferior pedicular cross member component 32. The voids within the superior pedicular cross member component 34 and the voids within the inferior pedicular cross member component 32 are preferably structured the same; and the cross member components are interchangeable. In an alternative embodiment, the voids within the superior pedicular cross member component may be different such as to provide different ranges of motion or other differing functional properties.

The cross member components may be installed in, e.g., a top-loading, drop-down method in the context of an open or semi-open procedure. The cross-member components may be gripped with a number of different tools and a number of different methods, including laterally, medially, etc., and the gripping tool may be configured such that the same can grasp non-parallel and/or non-linear cross member components. Moreover, the same should be capable of accommodating different spacings, from screw to screw, as screws are seldom parallel.

The strut system 40 includes a cylinder 42 coupled at one end to a spherical swivel or spherical element 44. In this way, the strut system can rotate about its longitudinal axis relative to the pedicular cross member components. The cylinder 42 is separated from the spherical swivel 44 by a stem 43. The spherical swivel 44 may be retained within the void, e.g., void 32b, by retaining ring 36 which may be disposed on the side of the spherical swivel 44 facing the stem 43. Moreover, the spherical swivel 44 may be somewhat flattened at its extremity, i.e., the extremity 36' opposite an extremity 45, so that the same does not extend beyond or out of the void 32b in the inferior pedicular cross member component 32. The retaining ring 36 engages a corresponding groove within the void. A similar retaining ring (not shown) may be disposed on the side of the spherical swivel 44 opposite the stem 43. However, generally, the spherical swivel 44 may be configured to rotatably sit within the void, and be constrained within the same once the retaining ring 36 is engaged.

The spherical swivel, which is a partially spherically shaped element, may allow for, e.g., about 8 o of polyaxial movement from the vertical, or a total of about 16 o from one side to another. Of course, even within the same device, different spherical elements or swivels may have differing degrees of movement as dictated by the requirements of the treatment. In one exemplary installation technique, the spherical swivel or element may be captured by the void such that the former may be initially installed in, or removed from, the latter at a predetermined angle, and then at other angles the former is prohibited from being removed from the latter. The predetermined angle may be chosen such that it is not an angle that is encountered in normal physical motion.

Within the cylinder 42 is disposed a cylindrical bushing 46 having a lip 47 annularly depending therefrom. The lip 47 engages a groove within the cylinder 42, where the groove is generally adjacent an extremity 45 of the cylinder 42. In this way, the cylindrical bushing 46 is secured within the cylinder 42. The cylindrical bushing 46 may be made, e.g., of a polymer material such as polyethylene, and provides an intermediate surface such that other elements do not deleteriously rub against the cylinder 42. One type of appropriate polymer material is Ultra High Molecular Weight Polyethylene (UHMWPE). PEEK may also be used, as may Acetal Copolymer (Delrin®) and Polyethylene. The material for the cylinder 42 may be, e.g., titanium or titanium alloy, stainless steel, or other such high-strength material.

Slidably disposed within the cylindrical bushing 46 is a strut assembly 50. The strut assembly 50 includes a grooved rod 48, which has parallel grooves 49 along at least a portion of an end. The grooves allow for a variety of sizes to be accommodated. The grooved rod 48 is partially disposed and concentric to an assembly 60. The grooved rod 48 is rotatably disposed within the assembly 60, i.e., is free to rotate about its longitudinal axis within the assembly 60.

The assembly 60 includes two attachment rings 62 and 64 as well as a spherical swivel section 52 which is configured to be disposed within the void, e.g., void 34a, in the superior pedicular cross member component 34. The spherical swivel section 52 may be constrained within void 34a by a retaining ring 56 which fits into the void 34a on one side of the superior pedicular cross member component 34, e.g., on the side facing the grooves on the rod 48. The spherical swivel section 52 is constrained within the void 34a translationally but only partially angularly, i.e., the section 52 may rotate and swivel, allowing for a variety of angles to be accommodated.

Figure 3:
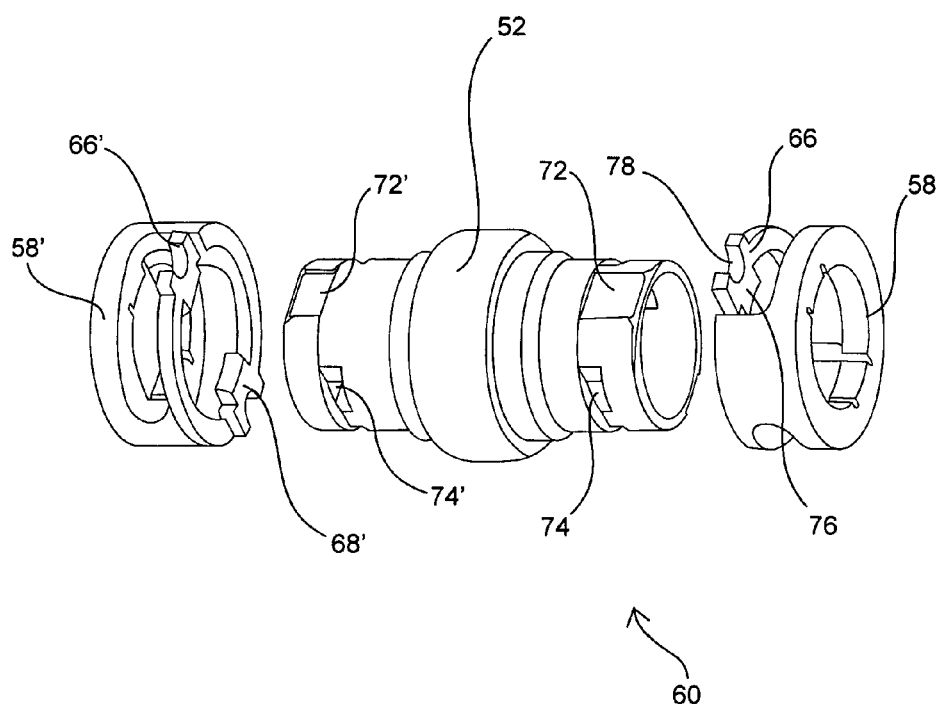
FIG. 3 illustrates additional features of a swivel and cap feature of FIG. 2.
Figure 4A:
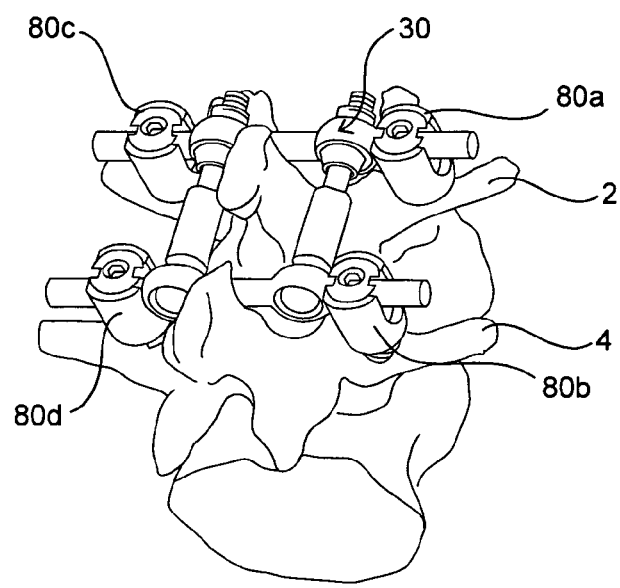
FIGS. 4A-4D illustrate trimetric, posterior, lateral, and caudad views, respectively, of the system of FIG. 2 implanted into a portion of a human spine such as is depicted in FIGS. 1A and 1B.
Figure 4B:
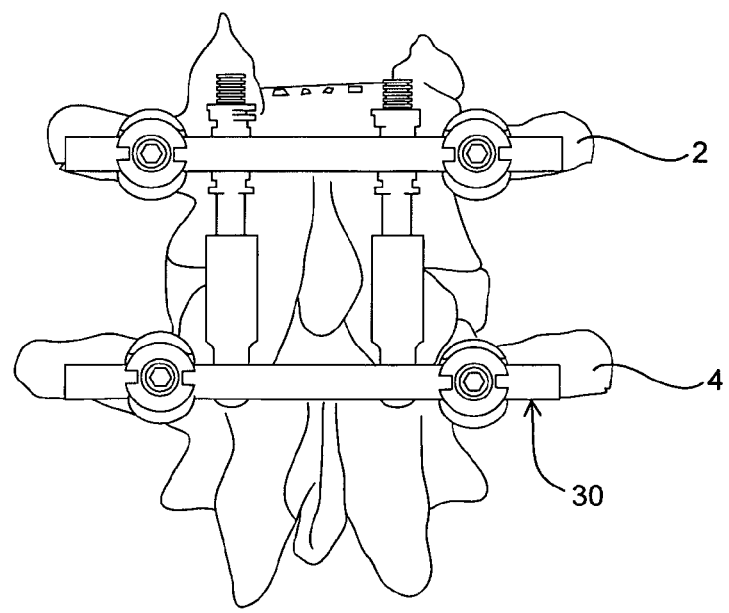
Figure 4C:
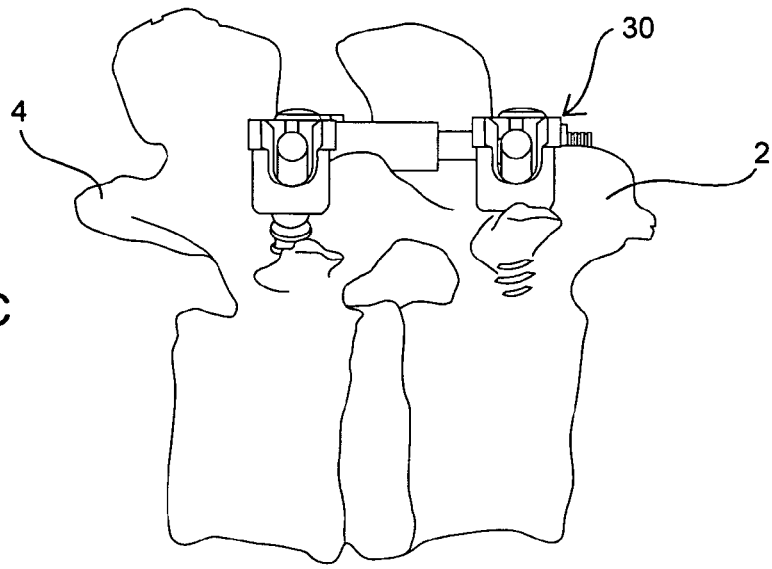
Figure 4D:
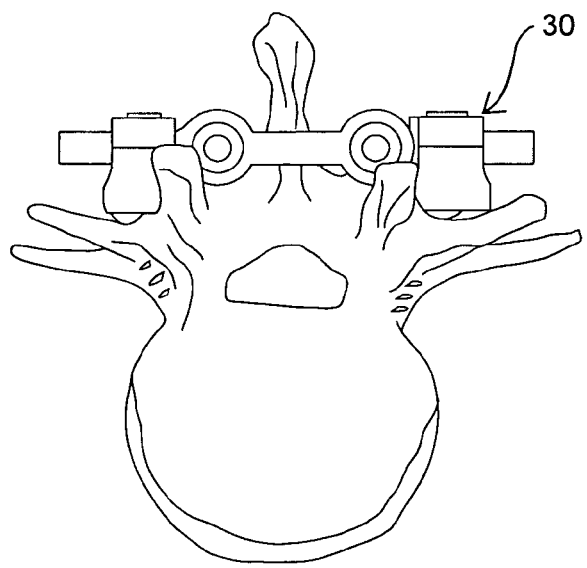

The operative length of the strut assembly 50 is set by placement of the cap 58 on one of the grooves. Cap 58 is shown in more detail in FIG. 3. Referring to the right-hand-side of the figure, cap 58 has diametrically opposing elements 66 and 68. Element 66 includes "U"-shaped element 78 and lug 76, with corresponding elements on element 68. In a post-installed use, the lug 76 extends through a channel 74 and into one of the grooves 49 on the rod 48 to lock the assembly 60 in one longitudinal position. To install, the lug 76 may be temporarily disposed on a flat 72, which means the lug 76 is not engaging any grooves 49, until such time as the lug 76 is disposed adjacent the desired groove 49. At this point, the cap 66 may be rotated, e.g., by a tool engaging "U"-shaped elements 78, and slightly longitudinally translated such that the lug 76 drops into the channel 74 and the desired groove 49. The lug 76 then locks the swivel section 52 onto one of the grooves 49. The description of the cap and its engagement on the left-hand-side of the figure is similar, and is shown in FIG. 3 with primed components.

Figure 5A:
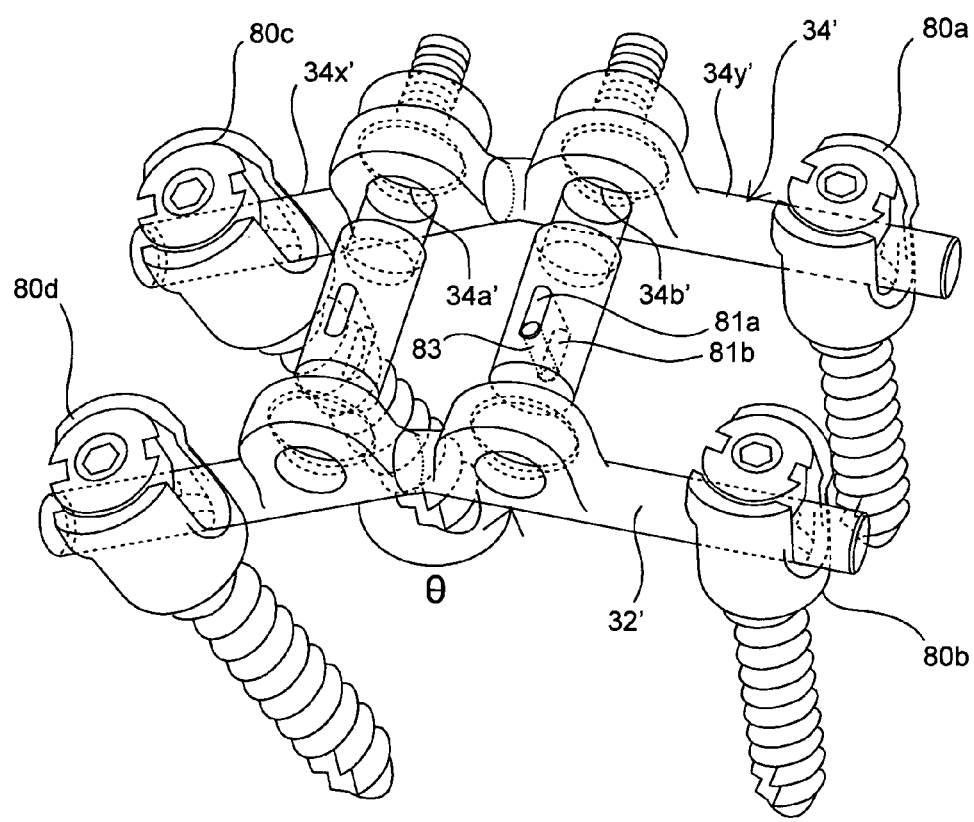
FIGS. 5A-5D illustrate trimetric views of another embodiment of a dynamic stabilization system of the present invention, showing in particular pedicle screws and strut systems.
Figure 5B:
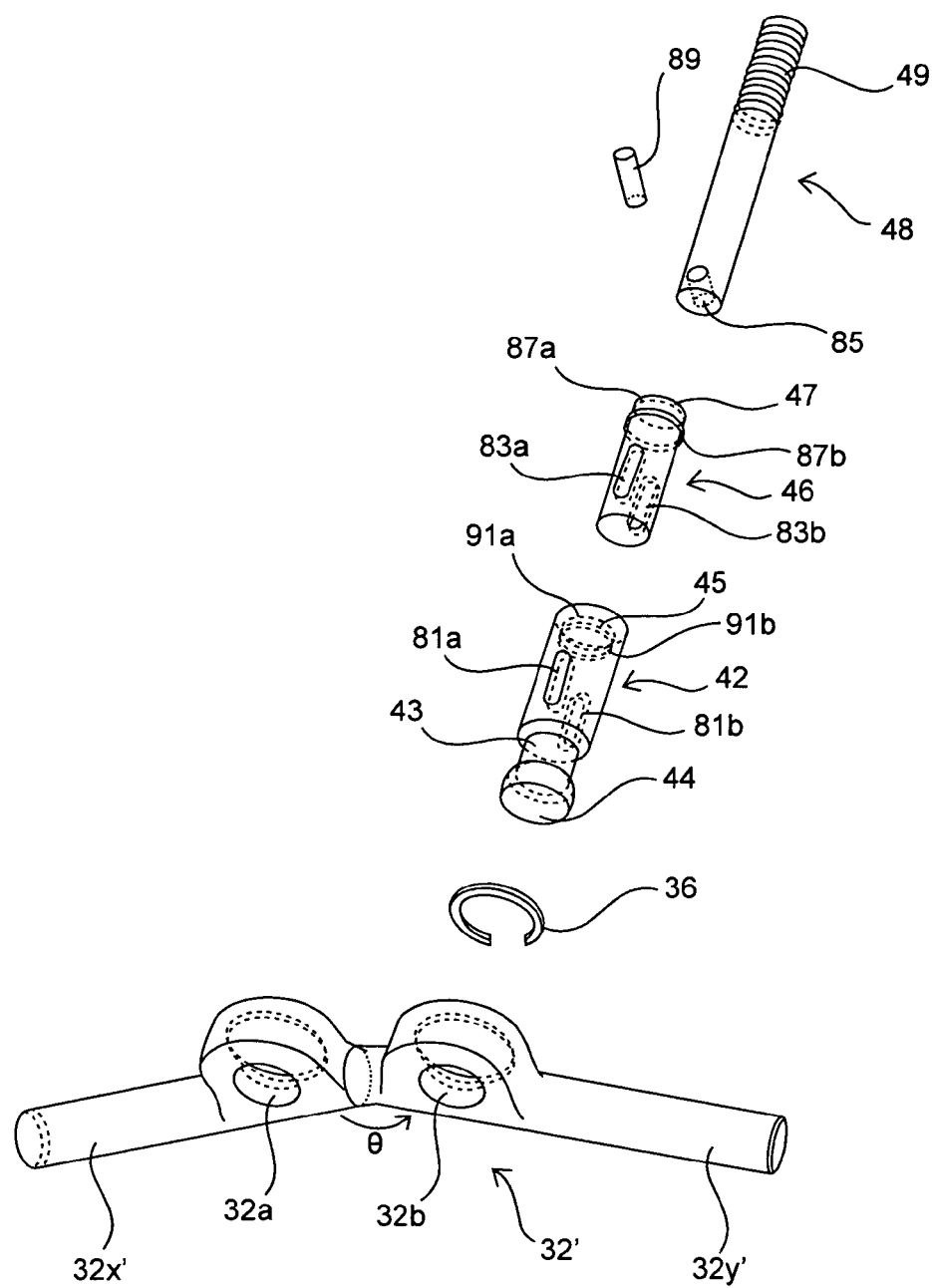

Besides a cap locking onto a groove, other method of securing the system may be employed. For example, a nut and screw threads may be employed in some embodiments, in which case rotation of the nut adjusts the maximum extension. In another embodiment, a plurality of through holes may be provided in the rod. A collar and/or pin, e.g., a cotter pin, may then be employed to lock the collar onto a particular through hole to set the length. Other such embodiments may also be envisioned. As noted, the minimum operative length of the strut assembly 50, and thus the minimum distance between the pedicular cross members (when the grooved strut 48 is within the bushing 46 as far as the same will go), is set by placement of the cap 58 on one of the grooves. This minimum distance should be set such that, when installed, the associated superior and inferior facet joints are not in contact or are in contact only by a predetermined amount. The maximum distance should be set such that, when installed and at the point of maximum extension, the grooved strut and the bushing should remain at least partially overlapping. This maximum extension may vary, but is chosen so as to limit the amount of extension according to the patient condition being treated. One way to limit the amount of extension is shown in FIG. 5B, where pin 89 engages holes 83a and 83b.

On the strut assembly or on the spherical swivels or elements may be disposed stops, such as eccentric stops, which allow more motion in one direction than another. Similarly, the opening in the void may be machined to limit motion in one or more different directions as well, e.g., by use of a slot-shaped opening, etc. In this way, the full rotatability of the system is compromised, but the resulting allowed motion better simulates typical patient back motion.

The stops or other motion-limiting features may also be made operator adjustable. That is, various operator-adjustable mechanisms such as operator-adjustable stops may be employed to vary the length or other dimension of the system, limit the resistance to motion, the limits on travel, etc. These types of mechanisms may allow adustability either pre-, peri-, or post-implantation procedure, and allow the system to be significantly customized for a given patient's anatomy.

FIGS. 4A-4D show various views of the system 30 as used to support one vertebrae relative to another. Also shown in these figures are four pedicle screws 80a-80d which are affixed to the pedicular cross members to hold the same onto the pedicles. In general, the pedicle screws attaching the superior pedicular cross member component are disposed at approximately the same level on the vertebra, and the same is true for those attaching the inferior component.

FIGS. 5A-5D show another embodiment of the stabilization device. In this embodiment, a superior pedicular cross member component 34' and an inferior pedicular cross member component 32' are shown affixed to pedicle screws 80a-

80*d*. In this embodiment, each cross member component is constituted by at least two lateral segments, e.g., superior pedicular cross member component 34' is made up of a first component 34*x*' and a second component 34*y*' which are not collinear but rather meet at an angle θ. Moreover, the centers of the voids 34*a*' and 34*b*' are no longer on the axes of the cross member components but rather are raised or translated posteriorly or dorsally relative to the patient's spine. Either or both of the angling of the cross members or the raising of the voids may be instituted in any given device according to embodiments of the invention. Both features have the advantage of moving the grooved ends of the grooved struts away from the spinous process and other vertebral features. To meet this objective, exemplary values for θ may be between about 0° and 135°, such as about 120°.

FIG. 5B shows a more detailed view of the strut system. Many of the components are similar to those described in FIG. 2, and only the changed components will be described here. In particular, the cylinder 42 is configured with opposing longitudinal slots 81*a* and 81*b*. Similarly, the bushing 46 is provided with opposing longitudinal slots 83*a* and 83*b*. The grooved strut 48 is configured with a thru-hole 85 at the end opposite the grooves 49. Once these components are assembled, a pin 89, whose length is greater than the diameter of the cylinder 42, may be press fit though hole 85 and slots 81*a*, 81*b*, 83*a*, and 83*b*. In this way, the length of slots 81*a*, 81*b*, 83*a*, and 83*b* limits the distance of travel of the pin 89 and thus of the grooved strut 48.

Another feature of FIG. 5B relates to the engagement of the bushing 46 with the cylinder 42. A lip 47 on bushing 46 is provided for mating with a groove 45 on cylinder 42. In FIG. 5B, a set of opposing pins 87*a* and 87*b* are also provided on or adjacent the end of bushing 46 for mating engagement with corresponding grooves 91*a* and 91*b* of cylinder 42. Of course, it should be clear to one of skill in the art given this teaching that any of the pins and grooves, or lips and grooves, may be switched without necessarily sacrificing utility or effectiveness. As above, it is also noted that the spherical swivel 44 may be somewhat flattened at its extremity to minimize the profile of the same.

Figure 5C:
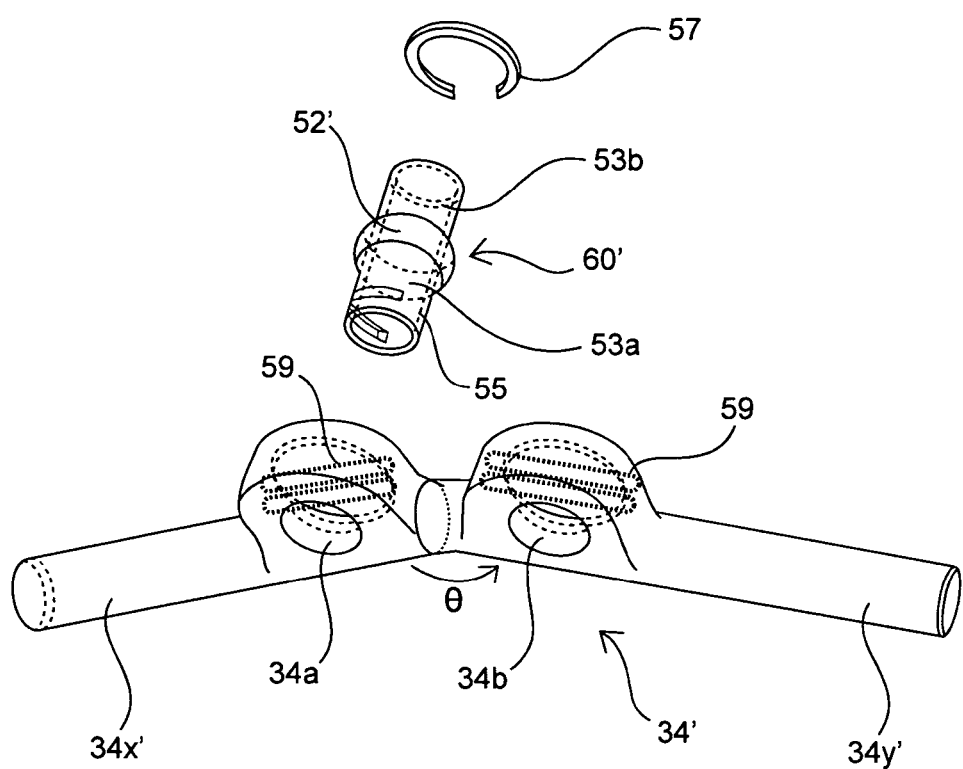

FIG. 5C shows in greater detail components connected to the superior pedicular cross member component 34. Many of the components are similar to those described in FIGS. 5A and 5B, and only the different components will be described here. An assembly 60' is shown having spherical swivel 52' and cylindrical ends 53*a* and 53*b*. The spherical swivel 52' forms an annular portion of a sphere. The cylindrical end 53*a* has at least one slot 55 formed therein. Through the slot 55, a retaining ring 57 may be disposed which holds the slot 55 and thus the assembly 60' secure at a particular groove 49 on the grooved strut 48. A longitudinal slot 59 formed in the pedicular cross member 34' allows a tool (not shown) to open and close the retaining ring 57 at the proper position.

Figure 5D:
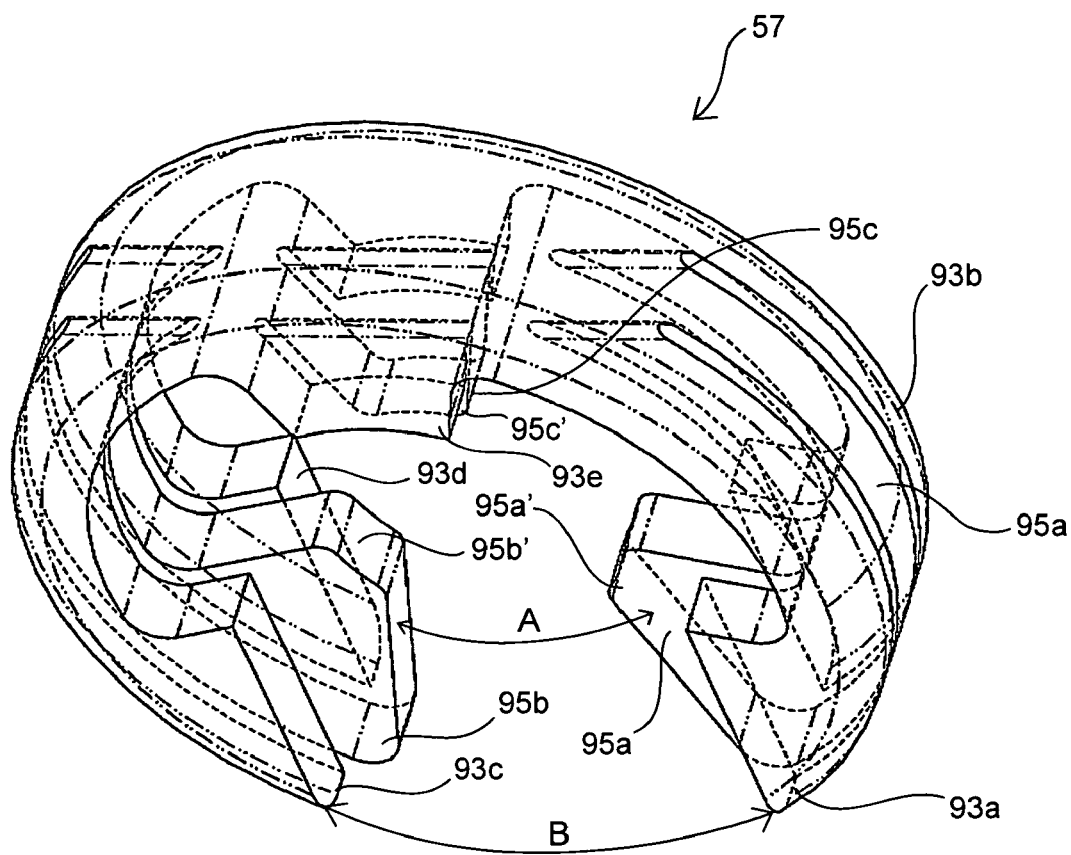

FIG. 5D shows a more detailed view of retaining ring 57. In particular, retaining ring 57 is configured such that a central annulus is partially defined in the ring. The central annular section has radial segments 95*a*', 95*b*', and 95*c*', that face inward towards the axis of the ring 57. The central annular section also defines a wedge-shaped void A. The lateral annula 93*a*-*e* (for clarity a reference numeral 93*f* is not indicated in the figure) define two wedge-shaped voids B (only one of which is indicated in the figure). Voids B are larger than void A, and as a result, extensions 95*a*-*c* extend generally into the center of the ring. The position of extensions 95*a* and 95*b* relative to lateral annula 93*a*-*e* may be changed by a tool (not shown) pushing on portions of the central annulus. Manipulated in this way, the retaining ring 57 and in particular extensions 95*a*-*c* may be disposed to hold the slot 55 and thus the assembly 60' secure at a particular groove 49 on the grooved rod 48.

Figure 6A:
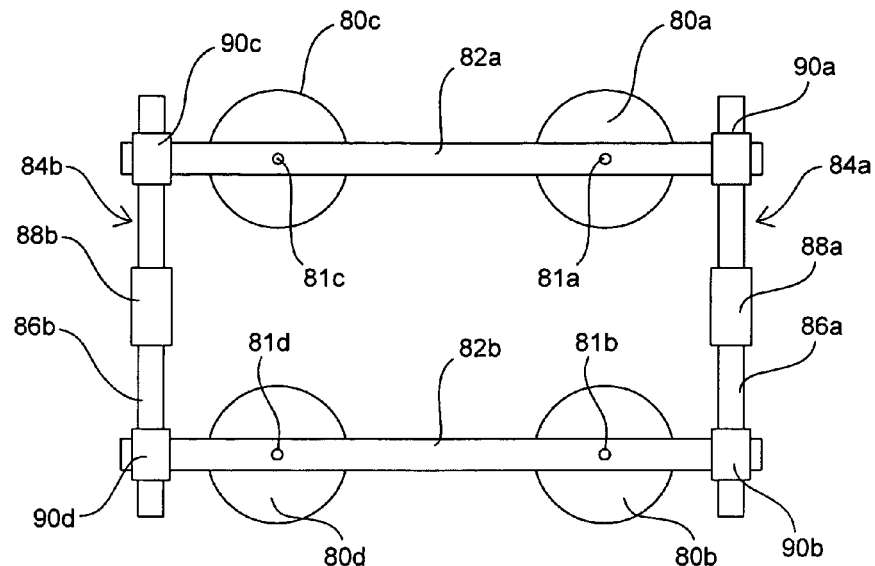
FIGS. 6A-6C illustrate posterior views of a related embodiment of a dynamic stabilization system of the present invention, showing pedicle screws and struts employing a dynamic member, as well as a multiple-level system in a rest position (B) and in a flexed position (C).

FIGS. 6A-6D show alternate combinations of various components described above. Referring in particular to FIG. 6A, a system is shown with four pedicle screw systems 80*a*-80*d*, affixed to pedicle cross members 82*a* and 82*b* via set screws 81*a*-91*d*. While the strut systems previously described were disposed between the pedicle screws, the strut systems in FIG. 6A are disposed external of the pedicle screws. That is, the distance between the pedicle screws is less than the distance between the strut systems (although it can also be greater than or equal to this distance). Swivel joints 90*a*-90*d* connect the pedicle cross members to the strut systems, each of which has a superior component 84*a* and 84*b* coupled to an inferior component 86*a* and 86*b* through a strut system including a shock absorber 88*a* and 88*b*.

Shock absorbers 88*a* and 88*b* may provide one or more functions. First, they may provide damped resistance to axial and/or torsional loads. They may also be operator-adjustable, either pre-, peri-, or post-implantation, both of their size and of their resistance to loading. Furthermore, they may accommodate length adjustments and/or range of motion adjustments.

Figure 6B:
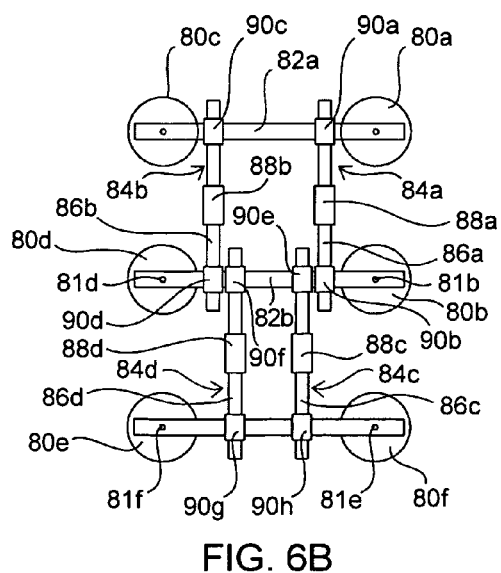
Figure 6C:
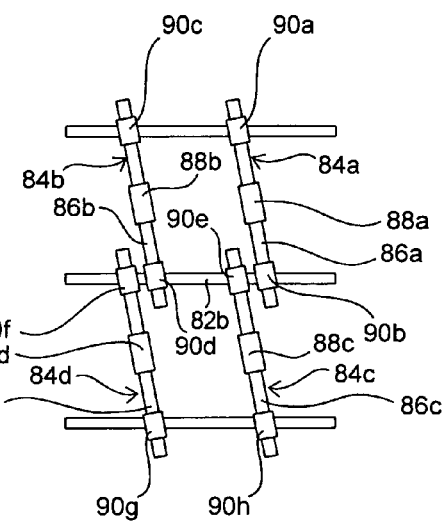

FIG. 6B shows a system similar to that of FIG. 6A but extended to multiple spinal segments. Similarly-numbered components refer to similarly-functioned components in FIG. 6A—only the letter suffix indexing the reference numeral has changed to represent the added components. In FIG. 6B, the strut systems are disposed interior of the pedicles, i.e., the distance between the strut systems is less than the distance between the pedicle screws. Also in FIG. 6B, the lower strut systems having shock absorbers 88*c* and 88*d* are disposed interior of the strut systems having shock absorbers 88*a* and 88*b*. FIG. 6C shows a system similar to that of FIG. 6B but where the lower strut systems having shock absorbers 88*c* and 88*d* are disposed such that shock absorber 88*c* is interior of shock absorber 88*a* and where shock absorber 88*d* is exterior of shock absorber 88*b*. Moreover, FIG. 6C shows the system where the struts are flexed in a leftward direction, as if the patient were performing a leftward bending motion of their spine.

Figure 7A:
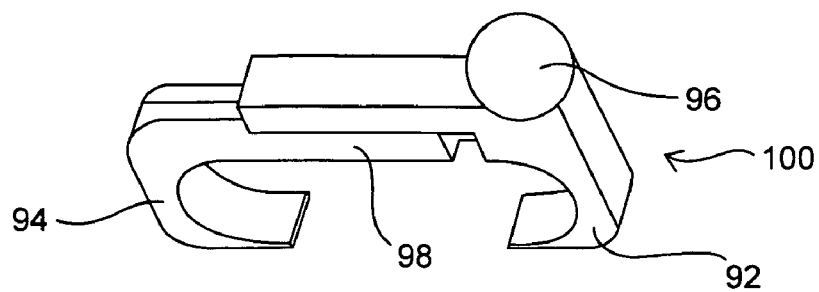
FIGS. 7A-7C illustrate perspective views of a further related embodiment of a dynamic stabilization system of the present invention, showing members that clamp onto parts of the vertebrae.
Figure 7B:
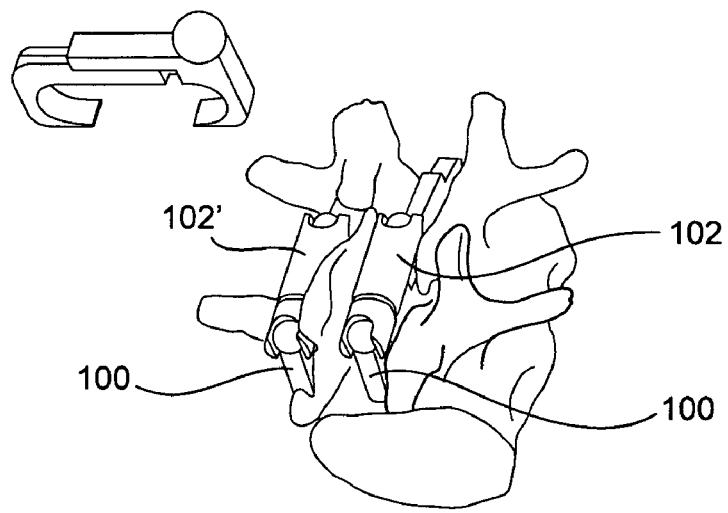
Figure 7C:
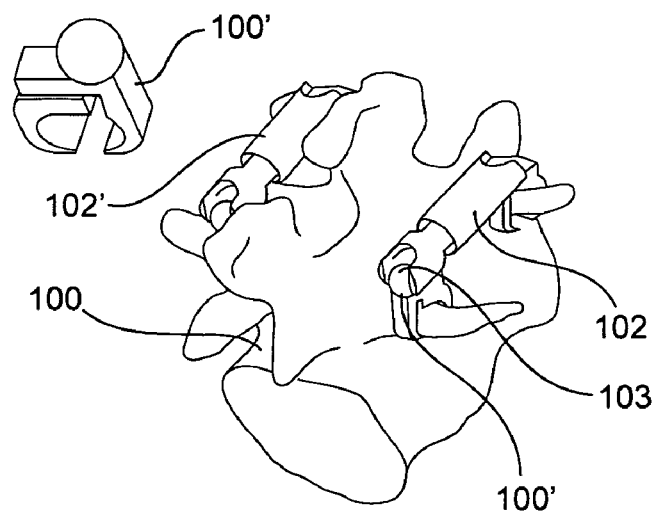

FIGS. 7A-7C illustrate an alternative embodiment according to the present invention. In this system, a clamp 100 is employed to attach a strut system, or a dynamic rod, to portions of the vertebra. In FIG. 7B, clamps 100 attach strut systems 102 and 102' to portions of a patient's lamina. In FIG. 7C, clamps 100' attach strut systems 102 and 102' to portions of a patient's transverse processes. In FIGS. 7B and 7C, clamps 100 and 100' differ primarily in size, as they are intended to attach to differently-sized spine features. However, one size, or an adjustable size component, may be used for all spine features, so long as the distance of travel allowed by the components allows for all spine features to be accommodated, i.e., affixed to.

Details of the clamp 100 are shown in FIG. 7A. A first component 92 is slidably attached to a second component 94 via attachment 98. The first and second components include "hook"-like features which mate well with spinal features. One or both of the first or second components has a ball end 96 affixed thereto to which an end of strut system 102, such as socket 103, may be attached. Attachment 98 may employ a tongue-and-groove system, with a set screw or other affixation tool, e.g., a tang, detent, ratchet, etc., used to maintain the relative position of the first and second components, once the optimum position is determined.

As in embodiments above, the ball end and socket may be such that the ball end may be initially installed in, or removed from, the socket at a predetermined angle, and then at other angles the former cannot be removed from the latter. In other words, the predetermined angle is chosen such that it is not an angle that will be encountered in normal physical motion. It should be noted that the ball end and socket, or other such attachment devices, can be disposed on opposite elements to those disclosed above. Moreover, the strut system in this embodiment has features similar to the strut systems in other embodiments, including use of a shock absorber. If two strut systems are employed, one on each side of an interspinous process, a cross-member component may be employed to connect the strut systems together.

Figure 8A:
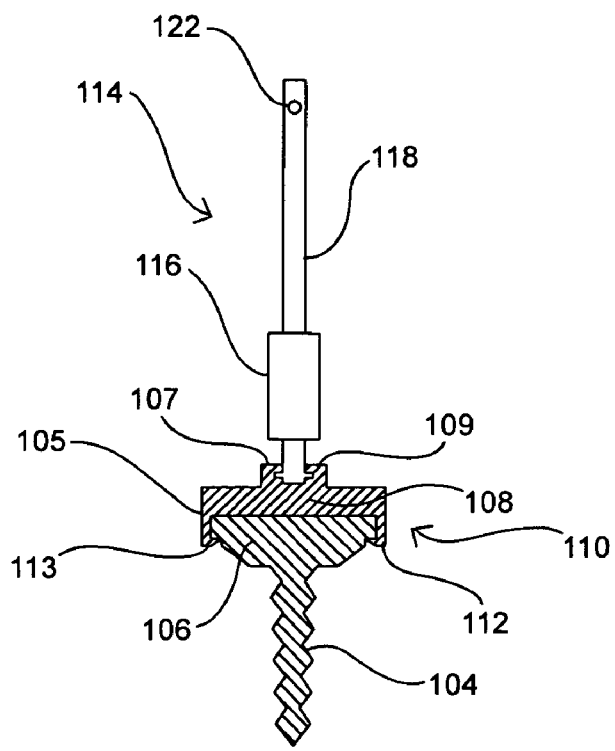
FIGS. 8A and 8B show cross-sectional side views of a further related embodiment of a dynamic stabilization system of the present invention, showing a pedicle screw system with a multiaxial pivoting arm or strut coupled to the same which can be rotated into place following installation into the pedicle.
Figure 8B:
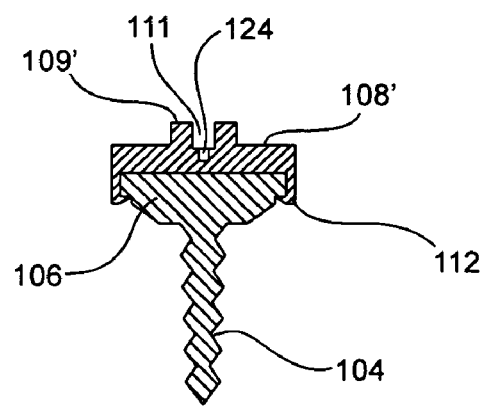

FIGS. 8A and 8B show a pedicle screw system 110 employing a rotating head with a hinged assembly having a pivoting arm. This embodiment allows rotation of the system after the screw is secured to the pedicle. In particular, the system 110 includes a screw thread 104, which is screwed into a pedicle, and which is attached to a head 106. A rotating hinged assembly 105 including a flat wall 108 and a downwardly-depending annular skirt 112 terminating at a lip 113. Lip 113 engages a corresponding wall on the head 106 to secure the assembly 105 to the head 106 and thus to the pedicle. The connection of the assembly 105 and the head 106 may be tight but loose enough to allow the assembly 105 to rotate relative to head 106.

Depending upwardly from wall 108 is a hinge assembly, which includes slots 109 which engage pins 107 attached at an end of a strut system, such as pivoting rod 114. The hinge assembly allows rotation of the pivoting arm relative to the wall 108 and other fixed components.

The pivoting rod 114 includes a straight section 118 and an adjustment element 116. The adjustment element 116 may allow for length adjustment, may act as a shock absorber such as a component configured to resist axial and/or torsional motion, may include a hydraulic assembly with a needle injection port to control the level of shock absorption, etc. FIG. 8A shows the pivoting rod with a single plane of rotation; however, multiple planes of rotation may also be provided for, as may also be provided for in the connection between the assembly 105 and the head 106. Moreover, "stops" may be provided to limit the range of motion of the pivoting arm, as well as to limit rotation between the assembly 105 and the head 106. Range of motion of pivoting rods, as well as motion between assembly 105 and head 106 may include a force resisting element, such as a spring component attached to resist axial and/or torsional motion. A hole 122 may be provided in the pivoting rod opposite the hinged end to receive a set screw securing the pivoting rod to a receiving assembly (not shown).

FIG. 8B shows a receiving cradle assembly that may be employed with the system of FIG. 8A. In this system, a recess 111 may be provided in the assembly 109' which depends upward from wall 108'. Recess 111 may hold the pivoting rod (not shown), and wall 108' may include a threaded hole 124 for securing the pivoting rod via a set screw, etc. In this FIG. 8B, the receiving cradle is rotatably attached to the pedicle screw. The pivoting rod is then captured by the cradle.

Figure 9:
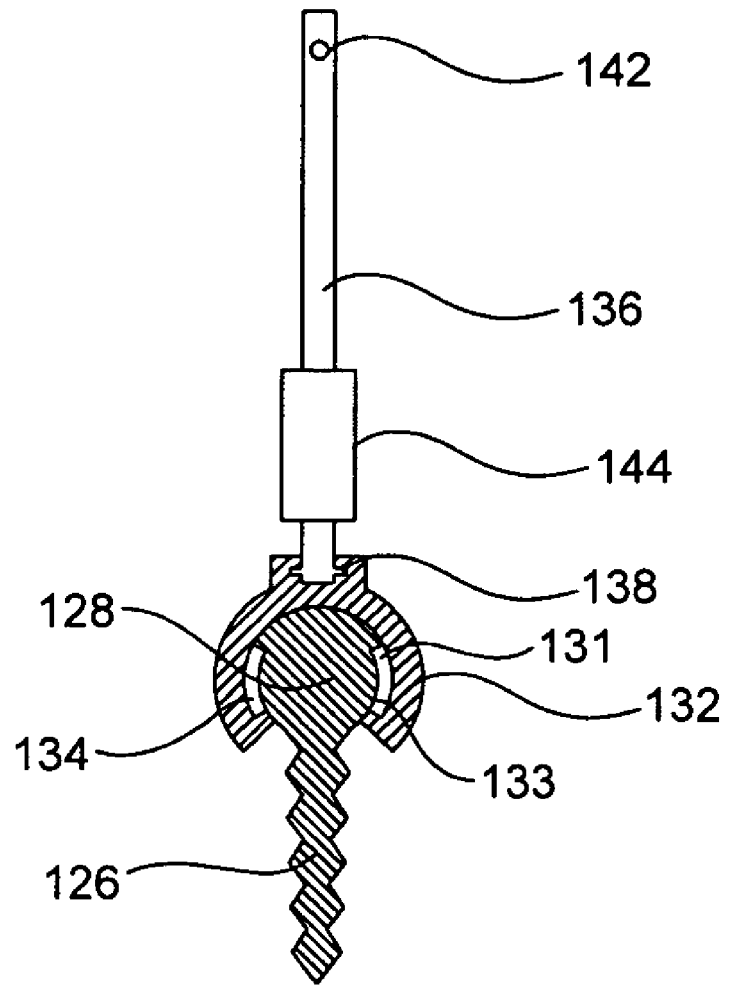
FIG. 9 illustrates a cross-sectional side view of a further related embodiment of a dynamic stabilization system of the present invention, showing a pedicle screw system with a pivoting arm or strut coupled to the same which can be rotated into place following installation into the pedicle.

FIG. 9 shows a system similar to that of FIG. 8A, having screw thread 126 attached to head 128. In this case, multiple planes of rotation are accommodated as head 128 is a ball disposed within a void 134 formed by socket assembly 132. A detent 131 is formed in head 128 which engages an abutment 133 such that over-rotation is inhibited. Multiple detents and abutments may be provided to inhibit over-rotation in other degrees of freedom, in this embodiment as well as in other embodiments, such as that shown in FIG. 8.

Depending upwardly from socket assembly 132 is hinge assembly 138 which is similar to the hinge assembly in FIG. 8A, and the discussion with respect to that figure is referred to for further explication.

As above, the pivoting rod includes a straight section 136 and an adjustment element 144. The adjustment element 144 is similar to the adjustment element 116 discussed above. A hole 142 may be provided in the pivoting rod opposite the hinged end to receive a set screw securing the pivoting rod to a receiving assembly (not shown but similar to the assembly of FIG. 8B).

The embodiment of FIG. 9 allows multiple planes of rotation to be accommodated following securement to the pedicle. The ball-and-socket arrangement may be replaced by a universal joint arrangement, or another other type of connection, as is true also of the other embodiments. Alternatively, rather than positioning the rotating joint on the pedicle screw side of the system, the same may be placed on the pivoting rod side of the system. Moreover, similar rotating joints may be disposed on the receiving assemblies. In a preferred embodiment, the rotating joints may encounter resistive forces such as those provided by a spring or frictional engagement between the interfacing components. In another preferred embodiment, these resistive forces are adjustable by an operator. In yet another preferred embodiment, the limits of travel of the rotation are adjustable by an operator.

Figure 10A:
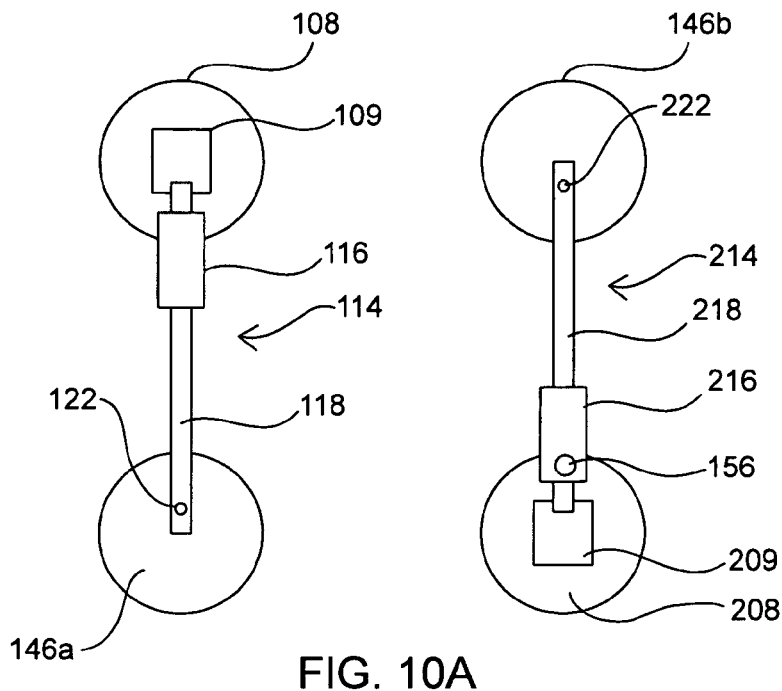
FIGS. 10A and 10B illustrate systems of FIGS. 8 or 9 rotated into receiving assemblies.
Figure 10B:
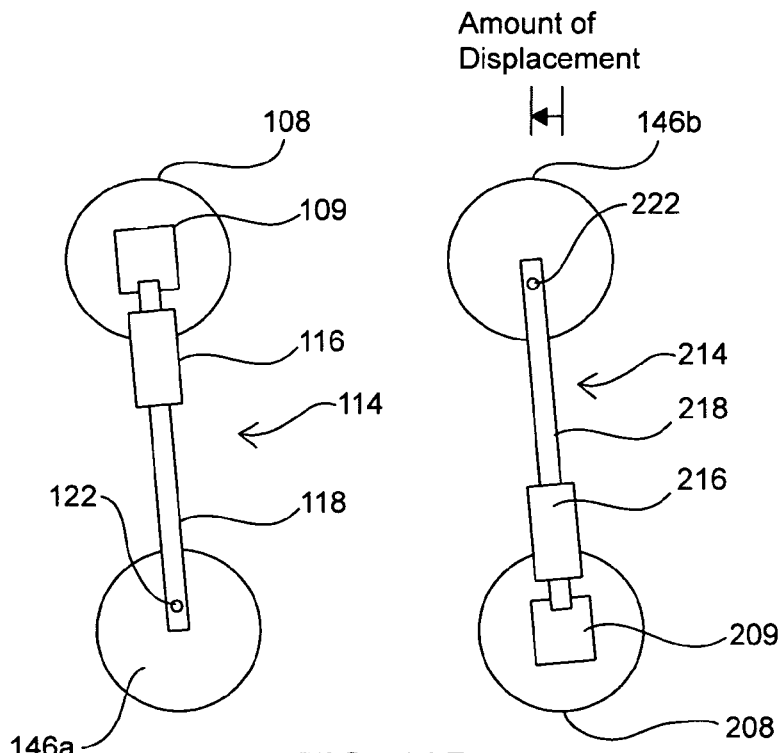

FIGS. 10A and 10B show systems consistent with FIGS. 8A and 9 rotated into receiving assemblies consistent with FIG. 8B. In particular, FIG. 10A shows the elements of FIG. 8A rotated into a receiving assembly 146a and secured thereto by a set screw through hole 122. On the right-hand side of FIG. 10A, corresponding elements are shown including wall 208, assembly 209, and pivoting rod 214 having straight section 218 and adjustment element 216, where the pivoting rod 214 is rotated and secured to receiving assembly 146b. The two complementary systems are shown in opposite orientations, although the same orientation could also be employed. Adjustment element 216 includes adjustment means 156, which may be employed to alter the length, resistance, or other features of the adjustment element 216. FIG. 10B shows the system of FIG. 10A following a head rotation of about 5 degrees, as may occur when a patient laterally bends their spine to the left.

Figure 11A:
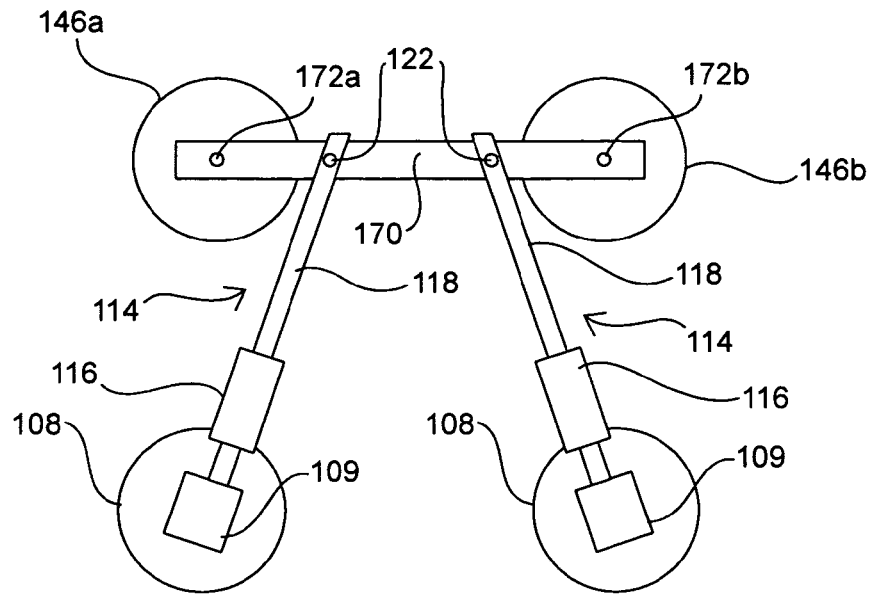
FIGS. 11A and 11B illustrate systems similar to those of FIGS. 10A and 10B but including a cross-bar.
Figure 11B:
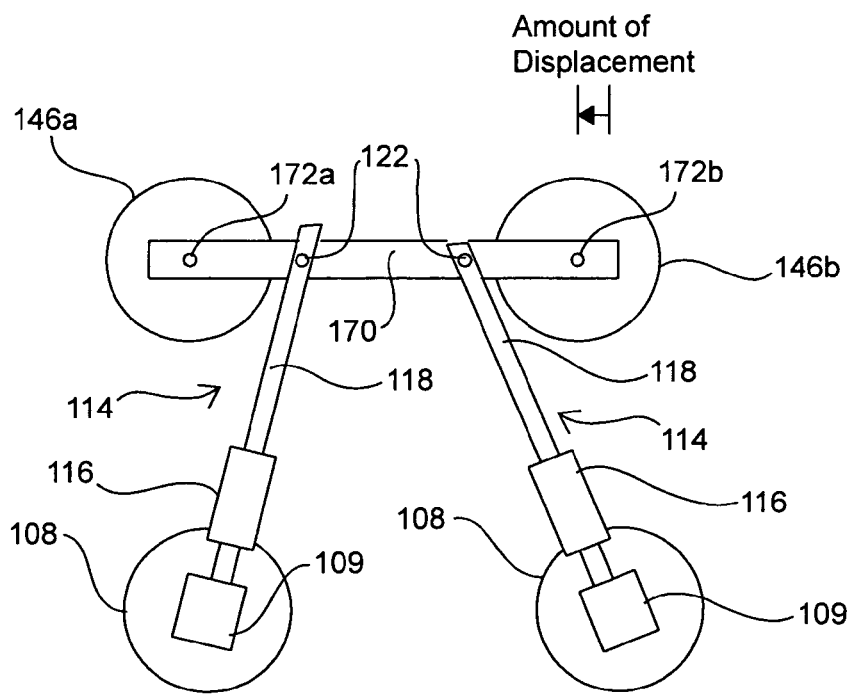

FIGS. 11A and 11B show systems consistent with FIGS. 8 and 9 rotated into a cross bar which is attached to two receiving assemblies. In particular, FIG. 11A shows the elements of FIG. 8A rotated into a cross bar 170 which is then attached at one end to a receiving assembly 146a via set screw 172a and at an opposite end to a receiving assembly 146b via set screw 172b. FIG. 11B shows the system of FIG. 11A following a head rotation of about 5 degrees, as may occur when a patient laterally bends their spine to the left. The use of a cross bar has certain advantages. In particular, the cross-bar in part serves to change where the points of rotation are and how forces are applied to the system. Also, if the crossbar was not present, as the patient moves, the screw heads associated movement may exert enough force on the pedicle screws to tend to cause loosening of the screws in the pedicle. By adding the crossbar from screw to screw, the screws become locked to each other in the same vertebra or at the same level. This way, when one vertebra moves relative to another, the motion placed on the rods does not inadvertently loosen the screws.

Figure 12A:
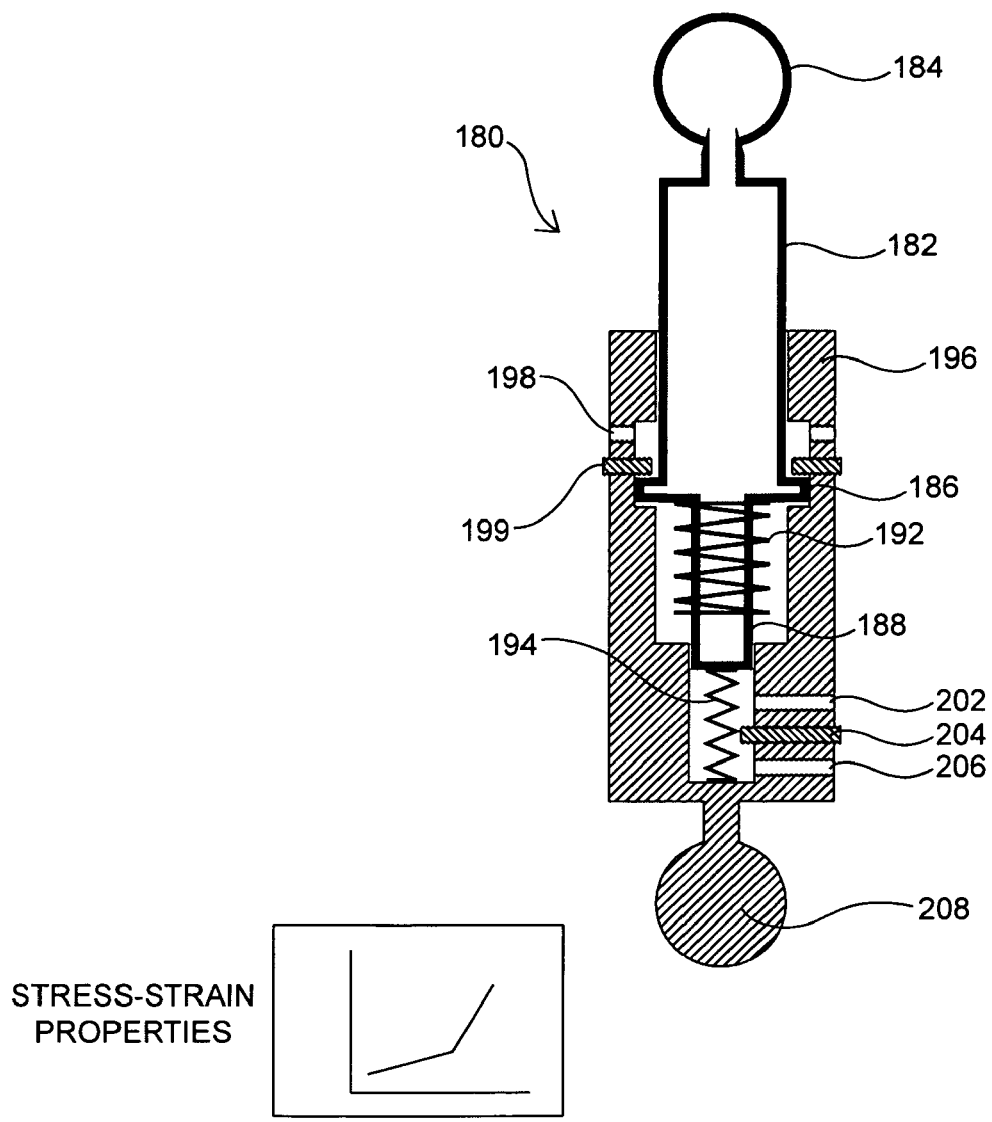
FIGS. 12A and 12B illustrate cross-sectional side views of an adjustable vertical distraction member having a minimum and maximum length adjustment.

FIG. 12A shows a side sectional view of a strut system 180. The strut system 180 has ball or swivel attachments 184 and 208 at each end, for connection to cross bars, cross members, pedicle screws, clamps, etc., as is known and has been described above. Swivel 208 is attached to the housing 196, and swivel 184 is attached to a piston member 182. Piston member 182 moves within the housing 196 and its motion is controlled by several factors, including: set screw 199, which may be placed as shown or in hole 198; set screw 204, which may be placed as shown or in any of holes 202 or 206; springs 192 and 194; and detents 186.

First, the placement of set screw 199 determines the travel of piston 182 since detent 186 cannot move past set screw 199. Second, the placement of set screw 204 determines the travel of piston 182 since the piston itself cannot move past set screw 204. A first spring 194, always attached to piston 182, directly determines the force on the piston 182. A second spring 192, shorter in its rest length than the entire travel of the piston and not attached at the end of the piston opposite ball 184, only engages when and after the piston moves a predetermined distance into the housing. In this way, the second spring 192 provides a heightened restoring force when the system is highly compressed. This in turn leads to a "two-step" resistance force indicated by the inset graph. While the springs in FIG. 12A are shown deployed in a longitudinal fashion, one or both may be replaced or complemented with torsional springs to provide not only an axial spring force but a torsional one as well. In some embodiments, the springs in FIG. 12A may themselves have ends that are bent or secured inside the housing to provide axial and torsional forces.

Figure 12B:
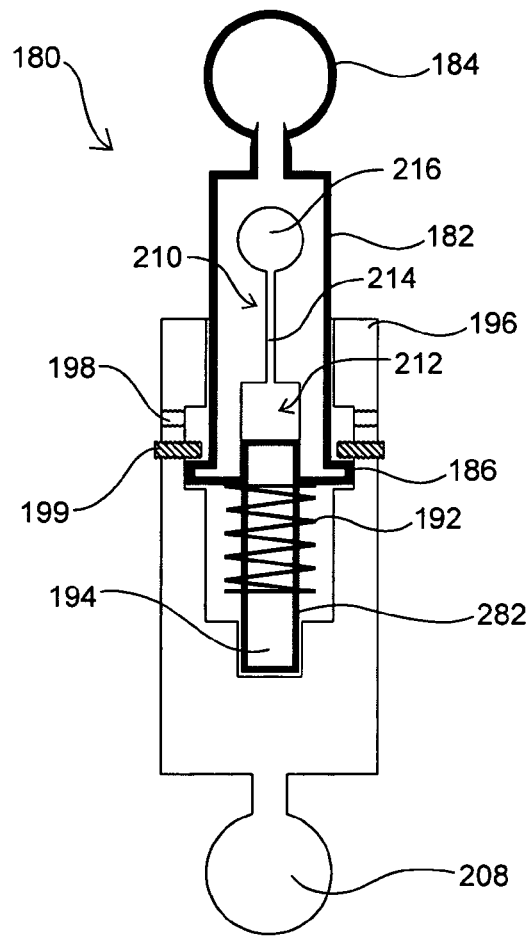

FIG. 12B shows a system similar to that of FIG. 12A, but with the first spring omitted and the set screw setting the lower limit replaced by a wall against which the piston abuts. The discussion with respect to common elements is not repeated, but the different elements are described here. The piston 182 includes an internal piston 282 which moves within a volume 212. Piston 282 is that which the second spring encircles. Internal piston 282 moves within volume 212 and is influenced by a hydraulic force disposed within the volume 212. For example, a hydraulic fluid may be disposed within the volume 212 and may be inserted therein via a needle injection port 216 coupled to the volume 212 via a channel 214. Alternatively, a set screw (not shown) may be employed to alter the volume or the amount of hydraulic fluid introduced.

Figure 12C:
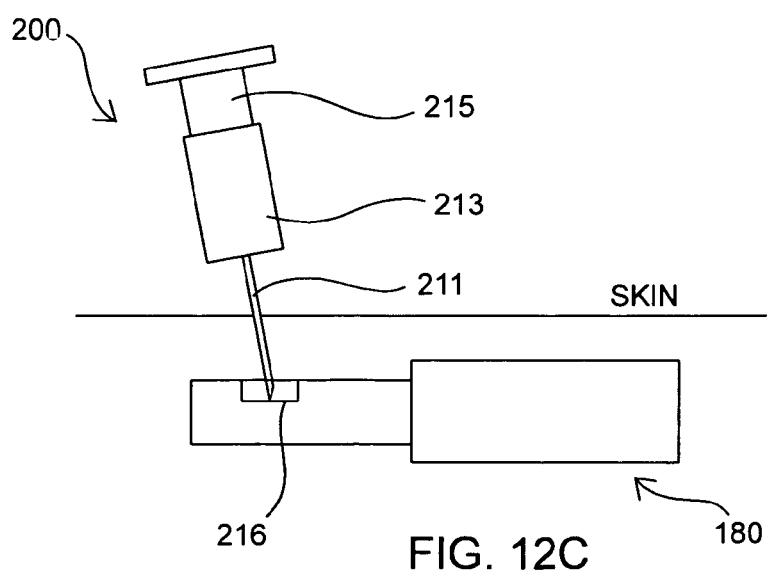
FIG. 12C illustrates a side view of a tool that may be employed to adjust the distraction of the member of FIG. 12B.

FIG. 12C schematically shows the system 180 implanted in a patient. The injection port 216 is shown being accessed by tool 200 including plunger 215, cylinder 213, and needle 211. The tool 200 and in particular the needle 211 can percutaneously penetrate the skin as shown. The location of the system 180 may be indicated via a marker, e.g., magnetic, ultrasonic, or radioopaque markers. The tool 200 can perform one or more functions such as to adjust the resistive forces of an implant, and/or adjust the distraction between two spinal motion segments by introducing or removing hydraulic fluid, or by adjusting a set screw to adjust the volume 212.

The pedicle screw systems which may be employed in embodiments of the present invention may include those disclosed in U.S. patent application Ser. No. 11/362,366, filed on Feb. 23, 2006, entitled "Systems and Methods for Stabilization of Bone Structures" and assigned to the assignee of the present invention. However, other systems may also be employed.

Figure 13A:
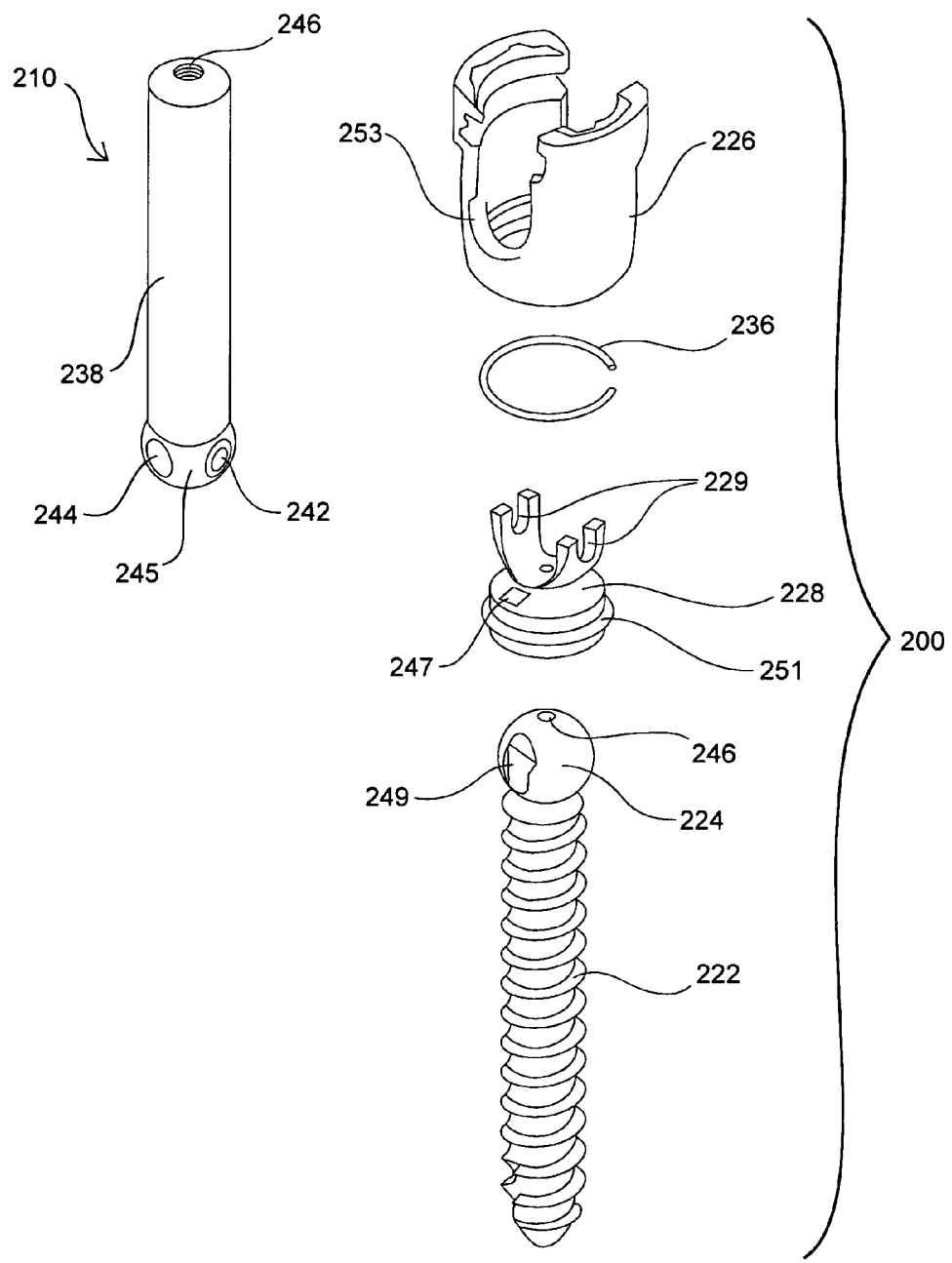
FIGS. 13A and 13B illustrate perspective exploded views of a pedicle screw head design that may be employed in the dynamic stabilization system of the present invention.
Figure 13B:
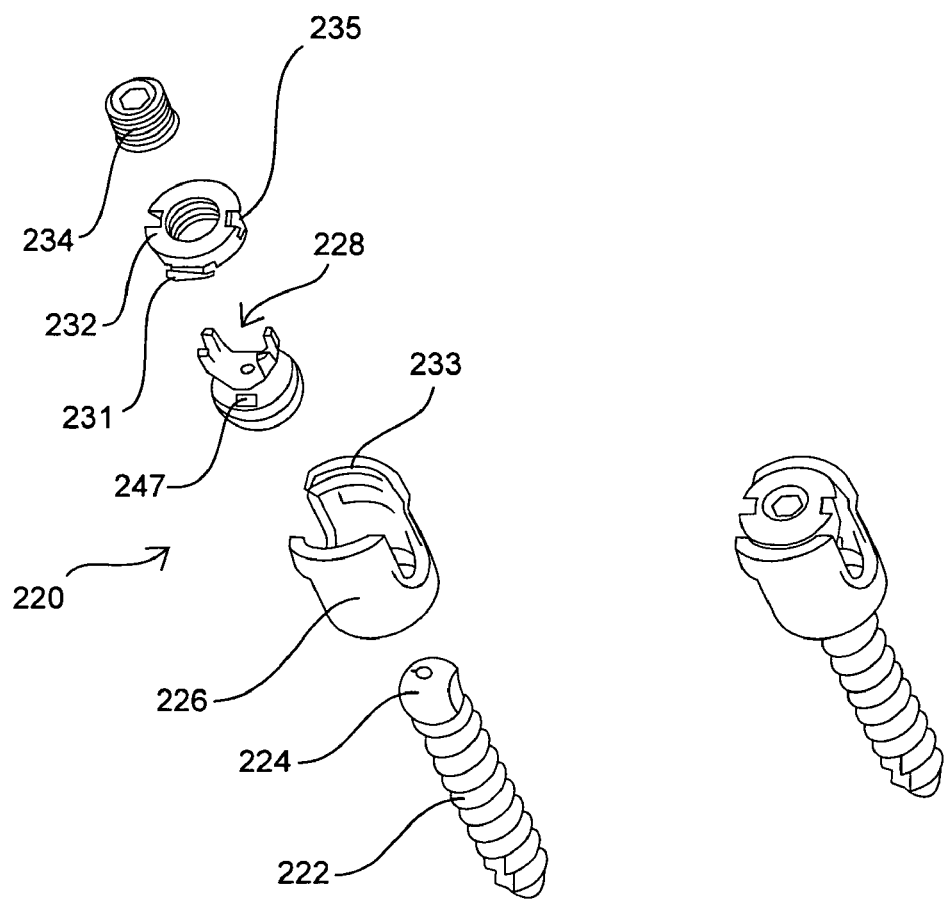

Referring in particular to FIGS. 13A and 13B, a device assembly 210 includes a pivoting rod 238 and a bone anchoring portion 200 including a polyaxial seat 226. A cannula 246 passes through rod 238 and through the bone anchoring portion 200 such that the assembly may be passed, in the orientation shown in the figure, into a patient through a installation cannula (not shown) and over a previously-placed guidewire, such as a "K-wire" commonly used in bone and joint procedures.

Figure 16:
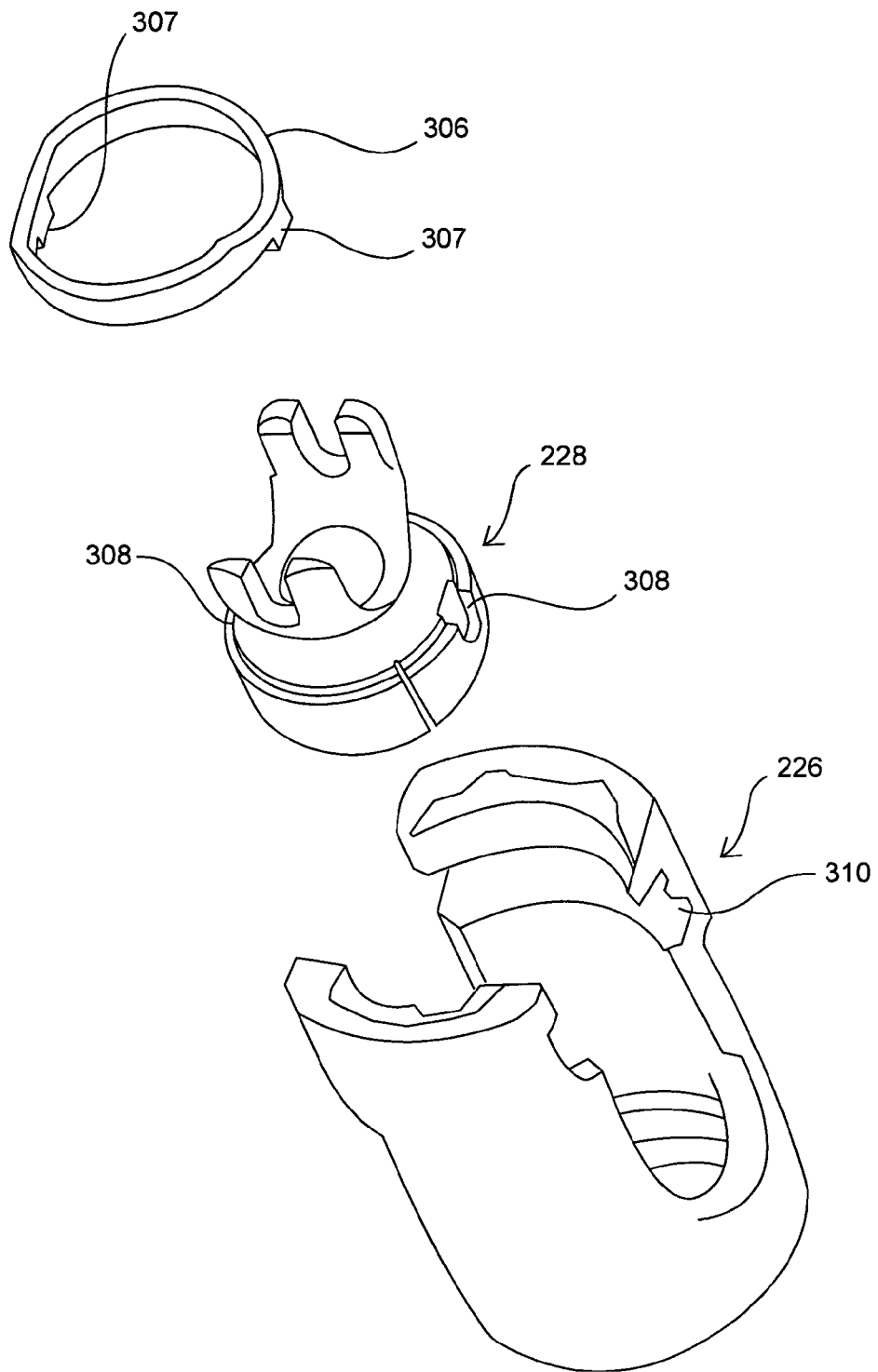
FIG. 16 illustrates details of a pedicle screw system which may be employed in embodiments of the present invention.

At one end of rod 238 is ball end 245, which is rotationally received and captured by a coupler 228. In particular, "U"-shaped grooves 229 are provided which mate with corresponding pins 242 on rod 238 to allow the rod 238 to be pivoted in a perpendicular (or other angular) fashion relative to the rest of the system. Referring to FIG. 16, coupler 228 may be attached to the seat 226 via a retaining ring 306 having lugs 307 which cooperatively and securely engage corresponding slots 308 in the coupler 228 (and may also engage slots in the seat). The retaining ring 306 is secured to the seat 226 via groove 310 formed in the cylindrical interior of the seat. In this way, the retaining ring and the coupler are press fit together into the seat. The coupler and seat have a keyway (not shown) such that they are aligned with one another. In this way, the coupler is prevented from being misaligned with the seat, and a separate tool is no longer required to align them to each other in order to insert the rod.

Figure 15:
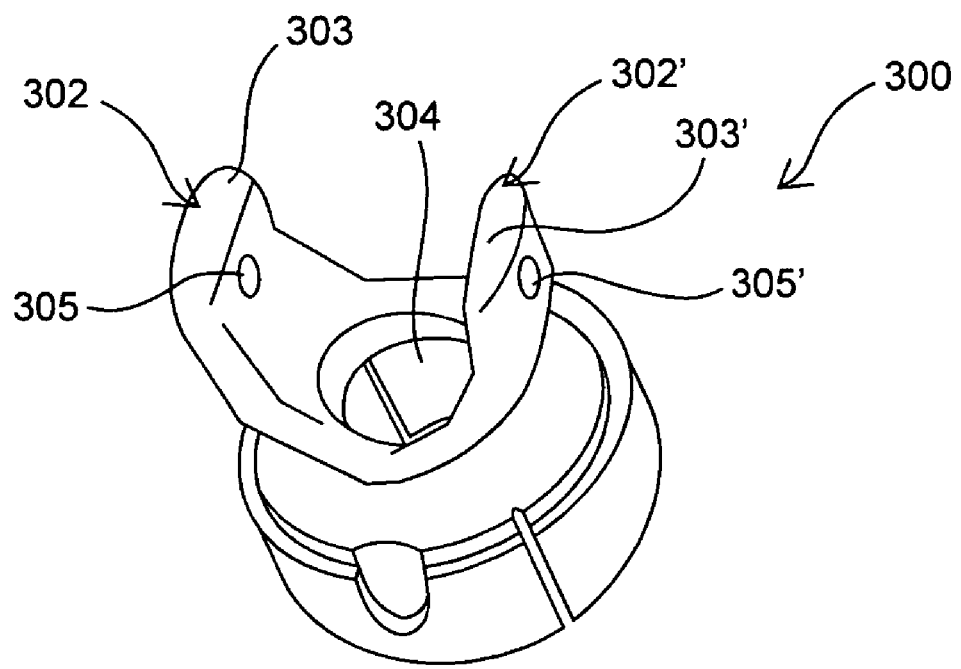
FIG. 15 illustrates a coupler for use in a pedicle screw system which may be employed in embodiments of the present invention.

In an alternative embodiment, as shown in FIG. 15, the "U"-shaped grooves 229 are replaced with a "closed" saddle having receivers 302 and 302'. In this case, during installation of the rod, the pins 242 on the rod 238 push on ramps 303 and 303' until the pins drop into holes 305 and 305'. Once the pins drop they are captured and generally require a tool for removal. In this way, the end of the rod cannot be displaced when the opposite end of the rod is being captured by a receiving assembly. In this embodiment, the rod is not attached to the coupler prior to installation. Because it not attached, the bone screw can be driven directly through a hole 304 in the coupler (no tangential rotation arrangement is necessary).

Returning to the embodiment of FIGS. 13A and 13B, the coupler mates with the ball end 224 in a snap-fit ball-and-socket arrangement. The screw-ball end-coupler system sits within seat 226 and is at least partially secured therein because coupler lip 251 rests on seat lip 253. The screw-ball end-coupler system may be further secured using retaining ring 236 on top of lip 251.

The rod 238 can be inserted into the saddle of coupler 228, which is assembled to the seat 226, by an operator, or may be provided in a pre-attached state. The arm 238 can be removable from coupler 228 which is assembled to the seat 226, or may be permanently, though rotatably, attached, whether provided in a "to-be-assembled" or a pre-assembled state. The ball and socket design of FIG. 13 allows multi-directional rotation of pivoting arm 238. Alternative designs may allow a single degree of freedom, or may allow more sophisticated trajectories of travel for the distal end of arm 238.

After the rod has been pivoted to a position for use in a patient, the rod may be held in that position by use of the closure element or cap 232 and a set screw 234. The closure element 232 may be snap-fitted into the seat 226 by interaction and engagement of closure element tabs 231 and seat grooves 233. Instead of grooves and tabs, lugs may also be employed. Lugs have the benefit of preventing the seat from splaying and releasing the rod. Furthermore, besides the snap-fit of closure element 232, the same may also be dropped in and captured with set screws or other capture devices. One particular other such capture device includes an integral locking nut/plug combination, which eliminates the need for a plug and set screw set.

A closure element slot 235 may be disposed in the closure element 232 so that the same may be further tightened along the groove 233 if the groove 233 is provided with a ramp system. Of course, various other techniques may also be used to keep closure element 232 within seat 226. The set screw 234 may then be tightened to secure the rod 238 against movement.

Except in arrangements such as that shown in FIG. 15, the screws such as screw 222 are generally driven into place in the bone when the rod 238 is in the position shown in FIG. 13A, that is, coaxial with respect to the axis of the screw thread. The top of the screw head 224 is then rendered inaccessible, although that is where slots for the driving of such screws are generally disposed. For this reason, at least one peripheral slot 247 in the coupler, a flat 249 in the screw head 224, and a flat 244 on the side of the rod 238 may be disposed so that a driver with a cooperating element may be used to rotate the screw 222

In one method of use, the screw 222, the coupler 228, the seat 226, the rod 238, and the corresponding intermediate elements are assembled prior to implantation in the patient. The device is inserted over the guidewire. The screw is then driven into the desired bone by use of a driver (not shown) generally having one or more protrusions which are long enough to pass through the seat 226, through intermediate elements, and to cooperatively engage with the flats 249. Any number of protrusions and flats may be employed. In certain embodiments, 2, 3, 4, 5, or 6 (for hex) flats and a corresponding number of protrusions on the driver may be employed. The flats may be equidistantly disposed about the screw head or may be otherwise disposed arbitrarily. Once the screw is driven into the bone, the rod is pivoted and the closure element and set screw applied.

In another method of use, the screw 222, the coupler 228, the seat 226, and the corresponding intermediate elements are assembled prior to implantation in the patient. The screw is driven into the desired bone by use of a driver which cooperatively engages with the hole 304 (see FIG. 15). Once the screw is driven into the bone, the rod is inserted, captured, and then may be pivoted and the closure element and set screw applied.

FIGS. 14A-14D show a "breakaway" minimally-invasive screw design. A screw 252 having a ball-shaped head 258 is disposed within a seat 262. The head 258 is connected via a breakaway stem 270 to a pivoting rod 264 having a proximal end 268 with a larger diameter than a hole 266 in the seat 262 through which the rod passes. When the system is initially assembled, a common guidewire cannula 254 extends through the components.

After installation, the pivoting rod 264 may be broken away from the head 258 at the breakaway stem 270. To perform this breaking away, the rod may be rotated about its axis while the screw is held (e.g., by the bone) or angled away from the axis of the screw 252. Once broken away, the pivoting rod 264 and seat 262 may move relative to the screw head 258, and in particular may be rotated such that a neck 257 disposed between screw head 258 and a lip 256 is disposed substantially within a void 274 formed in the seat 262. The void 274 has a smaller area than the cross-sectional area of the screw head 258 so that the seat 262 is substantially affixed to the screw head 258, at least within a normal or typical range of motion. By use of another void diametrically opposed to void 274, shown in FIG. 14D as void 274', a multi-level system may be provided, as a distal end 276 of an adjacent pivoting rod 278 may be engagingly disposed within the void 274'. In any case, the size of the opening 266 may be chosen so as to limit the angular travel of the pivoting rods to a predetermined desired amount.

In all cases, upon implant, the strut system can be selectively distracted or compressed to achieve the desired intervertebral spacing or distraction. As such, the length of the portion of the strut between the components may be adjusted to accommodate the natural and/or desired vertebral spacing, and provides sufficient flexibility, compression and distraction to accommodate and facilitate spinal motion.

Moreover, in this embodiment as well, the strut system may include a dynamic element along its length, e.g., to resist axial and/or torsional forces, and this dynamic element may be adjustable by the operator pre-, peri-, or post-implantation. The strut system may have a variable length or variable other dimension.

It is additionally noted that the break-away embodiment may be replaced with a frictional-engagement embodiment, in which the rod or strut system is frictionally engaged to the pedicle screw, but it not integral therewith. In this embodiment, the pivoting of the rod may cause the frictional engagement to be reduced or eliminated, e.g., via an eccentric feature that maximizes frictional engagement when the rod is aligned with the screw but reduces this frictional engagement as the rod becomes oriented at a 90 degree angle or pivot with respect to the screw.

Besides the pedicle screws disclosed above, other pedicle screws may be used with the present invention. For example, the screws may have a polyaxial configuration, as is commonly used in affixing implanted devices within the spine—e.g., rods and plates for fusion. These types of screw allow for customizing the position of the implants for the particular spinal anatomy. While conventional pedicle screws are suitable for use with the systems of the present invention, use of such screws may result in complications when used with dynamic stabilization systems that may not otherwise occur with fusion based systems since the former allows motion which, when repetitive, may result in complications at the screw bone interface, along the screw itself, or at the screw rod interface.

The subject devices and systems may be provided in the form of a kit which includes at least one pair of components that can be used on the left or right sides of the above described dynamic stabilization systems. As numerous applications require the treatment of more than one spinal segment or unit, the subject kits may include as many sets of components of the subject systems that may be used to treat the application hand. Typically, however, no more than about two to three sets are implanted in any one surgical application. The kits may further include pedicle screws for securing the above-described systems to the vertebral bodies as well as other instrumentation for implanting the systems. The screws may be pre-fixed to the respective superior and inferior components, or may be provided separate from these components and subsequently fixed to the components upon implantation into the vertebrae. Instructions for implanting the various devices and systems may also be provided with the kits. Such instructions may include, for example, the manner in which the interconnecting members of the system components are secured to the respective base members, and may further provide protocols for determining the most suitable length, stiffness/flexibility, shape or the compressive/distractive forces imposed on a strut member of the various system, and making adjustments to these characteristics accordingly. Such kits will also typically include strut systems of various sizes, and may further include devices such as guidewires, cannula, trocars, scopes, drug delivery devices, inflation devices, distraction devices, expandable devices, cutting instruments, holding devices for delivery, screwdrivers, or expansion media.

The devices and systems of the present invention may be implanted through open surgical approaches, limited open surgical approaches, minimally invasive approaches as well as percutaneous approaches. Generally, open placement or implantation of pedicle screw-based systems involves dissection of the tissue and fascia and may involve the removal of all of the posterior element or elements if not some of the posterior elements of the affected spinal segments—including the lamina, the spinous process, facet complex, and transverse processes. However, removal of some or all of these parts may not be necessary and is determined by the physician on a case-by-case basis.

With any approach, e.g., open, minimally invasive or percutaneous approach, after insertion of the pedicle screws, the stabilization system is inserted. The engagement between the system components and their respective screws may be accomplished in one of two ways. The connection between the screw and the system components may be prefabricated where the two are provided as an integral unit or the screws may be provided as modular components discrete from the system components.

For systems in which the length, stiffness, shape and/or positioning of the interface or strut member are not adjustable, fixation of the superior and inferior components to the vertebrae on both the left and right sides of the spinal motion segment substantially completes the implantation procedure. For those systems including such an adjustable interconnecting or strut member, the member is engaged with the superior and inferior components (as described above in the respective descriptions of these various systems) and its length, stiffness, shape and/or position is adjusted accordingly. A separate tool may be used to facilitate the adjustments. For example, a device may be employed to selectively tighten the strut segments. After the strut characteristics and features are confirmed, the strut is locked into place.

Distraction may occur prior to locking, such as via patient flexion or via a distraction device. The distraction device may be a balloon being inflated, and the same may be secured to portions of the superior and inferior vertebra or may be secured to installed pedicle screws or secured to other components between the pedicle screws.

The implantation procedure may be combined with other procedures, including fusion, dynamic stabilization, disk repair, disk augmentation, disk replacement, spinal stenosis repair, laminectomy, spondylolisthesis repair, fracture repair, tumor resection, and vertebral repair. The devices according to embodiments of the present invention may also be used to replace prior-installed devices, or stabilization rods may be employed to replace prior-installed embodiments of the present invention.

The preceding merely illustrates the principles of the invention. It will be appreciated that those skilled in the art will be able to devise various arrangements which, although not explicitly described or shown herein, embody the principles of the invention and are included within its spirit and scope. For example, while a rotatable strut system is shown, the same type of rotatable segment may be accomplished using a universal joint system. Moreover, the strut system and cross member components disclosed herein may be made entirely adjustable as described, and may be adjusted before, during, or after implantation. While the strut systems have been disclosed to be straight, they may also be curved to more closely simulate the curvature of the spine to help facilitate the alignment of the screw heads for rod insertion, and may accommodate shock-absorber type constructions. In most cases, the strut systems should be made to allow flexion and extension of vertebra. The strut systems have been disclosed as having the potential to act as shock absorbers, and it should be understood that such shock absorber designs may include spring-loading, multiple springs to provide different distraction forces, torsional springs, and may also be provided with an elastic memory alloy that is sensitive to temperature change where the shape changes to a preformed shape to "close" or "tighten up", or other types of temperature sensitive materials, e.g., a Nitinol alloy, so that the same "warms up" over time, similar to the way a natural bone and ligament would. Other structures may be attached to either the cross member components or the strut systems, such as artificial facets or artificial interspinous processes, etc. Coatings or reservoirs or radioactive seeds may be provided on or in the cross member components or the strut systems to promote or prevent ingrowth, prevent infection, provide an anti-rejection functionality, etc. Threaded holes may be provided in the cross member components or the strut systems to allow the same to interconnect to other systems and devices, including another facet augmentation device. While the cross member components have been shown herein as having a length so as to traverse at least the width of a vertebra, such length is not required. The cross member components may be very small, e.g., defining only one void, and in this case only one strut system would be required. While the rod has been disclosed as being cannulated to allow attachment of the rod to the coupler prior to implantation, in many situations it is desired to attach the rod following implantation. In this case, no cannulation is then required.

Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A strut system configured to extend between a superior and inferior pedicular cross member component, the strut system including an adjustable vertical distraction member having a minimum length and a maximum length, comprising:

a first attachment element configured to connect with one of the superior and inferior pedicular components during use, the first attachment element including a receiving portion;

a second attachment element configured to connect with the other of the superior and inferior pedicular components during use, the second attachment element including a piston partially disposed within an interior of and concentric to the receiving portion of the first attachment element during use, wherein the piston is configured to travel longitudinally within the interior of the receiving portion during use, and wherein a distal end of the piston includes a detent; and a retaining mechanism configured to engage the detent of the piston during use to inhibit longitudinal movement of the piston, thereby limiting a longitudinal travel distance of the piston within the receiving portion, wherein the retaining mechanism is selectively positionable in one of at least a first discrete position and a second discrete position, wherein the retaining mechanism limits the longitudinal travel of the piston to a first distance when positioned in the first discrete position and limits the longitudinal travel of the piston to a second distance greater than the first distance when positioned in the second discrete position, and wherein the receiving portion has an exterior wall and wherein the retaining mechanism comprises a pin member extending through the wall into an interior of the receiving portion.

2. The strut system of claim 1 wherein the superior and inferior pedicular components are superior and inferior cross member components.

3. The strut system of claim 1 wherein the receiving portion is a cylindrical housing having a hollow interior section.

4. The strut system of claim 1 wherein the retaining mechanism is aset screw.

5. The strut system of claim 1 wherein the piston is moveable longitudinally from at least a first position to a second position during use.

6. The strut system of claim 1, further comprising an internal piston concentric with the piston and the receiving portion, the internal piston positionable at the distal end of the piston of the second attachment element and contained within the receiving portion of the first attachment element.

7. The strut system of claim 6 wherein the distal end of the piston includes a recess configured to partially receive the internal piston.

8. The strut system of claim 6, further comprising a second retaining mechanism configured to releasably engage the internal piston wherein the second retaining mechanism is selectively positionable in one of at least a first discrete position and a second discrete position, wherein the second retaining mechanism limits the longitudinal travel of the internal piston to a first distance when positioned in the first discrete position and limits the longitudinal travel of the internal piston to a second distance greater than the first distance when positioned in the second discrete position.

9. The strut system of claim 6 further comprising a spring having a larger internal diameter than an external diameter of the internal piston, and wherein the spring is disposed concentrically about the exterior of the internal piston such that the spring during use such that the spring encircles the internal piston, and wherein the spring is configured to at least partially restrict longitudinal movement of the piston relative to the housing.

10. A strut system configured to extend between a superior and inferior pedicular component, comprising:
   a first attachment element configured to connect with one of the superior and inferior pedicular components during use, the first attachment element having a proximal end and a distal end, wherein the proximal end has a swivel attachment and the distal end has a receiving portion;
   a second attachment element configured to connect with the other of the superior and inferior pedicular components during use, the second attachment element having a proximal end and a distal end, wherein the proximal end has a swivel attachment;
   a first piston partially disposed within and concentric to the receiving portion of the first attachment element, wherein a distal end of the first piston is at least partially contained within the receiving portion of the first attachment element, wherein the first piston is configured to travel longitudinally within the interior of the receiving portion during use, and wherein the portion of the first piston of the first attachment element at least partially contained within the receiving portion of the first attachment element includes a detent;
   an engagement element configured to engage the detent of the first piston during use to inhibit longitudinal movement of the piston, thereby limiting a longitudinal travel distance of the first piston within the receiving portion;
   a retaining mechanism selectively positionable in one of at least a first discrete position and a second discrete position, wherein the retaining mechanism limits the longitudinal travel of the first piston to a first distance when positioned in the first discrete position and limits the longitudinal travel of the first piston to a second distance greater than the first distance when positioned in the second discrete position; and
   a second piston fully disposed within and concentric to the receiving portion of the first attachment element, the second piston having a diameter less than a diameter of the first piston, wherein the first piston includes a recess at a distal end configured to partially receive the second piston.

11. The strut system of claim 10 wherein the receiving portion is a cylindrical housing having a hollow interior section.

12. The strut system of claim 11, further comprising an internal spring concentric with the housing, the first piston and the second piston, the internal spring having a larger internal diameter than an external diameter of the second piston, and wherein the spring is disposed concentrically about the exterior of the second piston during use such that the spring encircles the second piston.

13. The strut system of claim 12, further comprising a second spring concentric with the housing, the first piston and the second piston, the second spring having a smaller diameter than the diameter of the second piston, and wherein the second spring extends longitudinally from an end of the second piston and is retained in a second recess portion of the first attachment element.

14. The strut system of claim 10, further comprising an engagement element configured to engage the second piston during use to inhibit longitudinal movement of the second piston, thereby limiting a longitudinal travel distance of the second piston within the receiving portion, wherein the retaining mechanism is selectively positionable in one of at least a first position and a second discrete position, wherein the retaining mechanism limits the longitudinal travel of the second piston to a first distance when positioned in the first position and limits the longitudinal travel of the second piston to a second distance greater than the first distance when positioned in the second position.

15. The strut system of claim 10 wherein the engagement element is a set screw.

16. A dynamic stabilizing system configured to be coupled between a first vertebra and a second vertebra of a human spine, the dynamic stabilizing device comprising:
   a first member configured to be coupled to the first vertebra during use, wherein the first member comprises a wall defining a longitudinal recess;
   a second member configured to be coupled to the second vertebra during use, wherein the second member comprises:
      an elongated protrusion configured to be disposed within the longitudinal recess of the first member during use; and
      a detent feature extending radially from the longitudinal protrusion,
      wherein the elongated protrusion is configured to travel longitudinally within the longitudinal recess to facilitate movement of the first vertebra relative to the second vertebra during use; and a retaining mechanism comprising a member extending through a hole in the wall and into an interior of the receiving portion during use, such that at least an end portion of the member enages the detent of the second member to at least partially inhibit longitudinal movement of the elongated protrusion within the longitudinal recess during use, thereby limiting a longitudinal travel distance of the longitudinal protrusion within the longitudinal recess during use, wherein the retaining mechanism is selectively positionable in either one of a first discrete position and a second discrete position, wherein the retaining mechanism limits the longitudinal travel of longitudinal protrusion within the longitudinal recess to a first distance when positioned in the first discrete position and limits the longitudinal travel of longitudinal protrusion within the longitudinal recess to a second distance greater than the first distance when positioned in the second discrete position.

17. The dynamic stabilizing system of claim 16 further comprising a spring disposed about a circumference of at least a portion of the elongated protrusion, wherein longitudinal movement of the elongated protrusion within the longitudinal recess is configured to engage the spring to at least partially inhibit movement of the first member relative to the second member.

18. A strut system configured to extend between a superior and inferior pedicular cross member component, the strut system including an adjustable vertical distraction member having a minimum length and a maximum length, comprising:
  a first attachment element configured to connect with one of the superior and inferior pedicular components during use, the first attachment element including a receiving portion;
  a second attachment element configured to connect with the other of the superior and inferior pedicular components during use, the second attachment element including a piston partially disposed within an interior of and concentric to the receiving portion of the first attachment element during use, wherein the piston is configured to travel longitudinally within the interior of the receiving portion during use, and wherein a distal end of the piston includes a detent;
  an internal piston concentric with the piston and the receiving portion, the internal piston positionable at the distal end of the piston of the second attachment element and contained within the receiving portion of the first attachment element; and
  a retaining mechanism configured to engage the detent of the piston during use to inhibit longitudinal movement of the piston, thereby limiting a longitudinal travel distance of the piston within the receiving portion, wherein the retaining mechanism is selectively positionable in one of at least a first discrete position and a second discrete position, wherein the retaining mechanism limits the longitudinal travel of the piston to a first distance when positioned in the first discrete position and limits the longitudinal travel of the piston to a second distance greater than the first distance when positioned in the second discrete position.

19. The strut system of claim 18 wherein the receiving portion has an exterior wall and wherein the retaining mechanism comprises a pin member extending through the wall into an interior of the receiving portion.

20. The strut system of claim 18 wherein the superior and inferior pedicular components are superior and inferior cross member components.

21. The strut system of claim 18 wherein the receiving portion is a cylindrical housing having a hollow interior section.

22. The strut system of claim 18 wherein the retaining mechanism is a set screw.

23. The strut system of claim 18 wherein the piston is moveable longitudinally from at least a first position to a second position during use.

24. The strut system of claim 18 wherein the distal end of the piston includes a recess configured to partially receive the internal piston.

25. The strut system of claim 18 further comprising a second retaining mechanism configured to releasably engage the internal piston wherein the second retaining mechanism is selectively positionable in one of at least a first discrete position and a second discrete position, wherein the second retaining mechanism limits the longitudinal travel of the internal piston to a first distance when positioned in the first discrete position and limits the longitudinal travel of the internal piston to a second distance greater than the first distance when positioned in the second discrete position.

26. The strut system of claim 18 further comprising a spring having a larger internal diameter than an external diameter of the internal piston, and wherein the spring is disposed concentrically about the exterior of the internal piston such that the spring during use such that the spring encircles the internal piston, and wherein the spring is configured to at least partially restrict longitudinal movement of the piston relative to the housing.

27. A strut system configured to extend between a superior and inferior pedicular component, comprising:
  a first attachment element configured to connect with one of the superior and inferior pedicular components during use, the first attachment element having a proximal end and a distal end, wherein the proximal end has a swivel attachment and the distal end has a receiving portion;
  a second attachment element configured to connect with the other of the superior and inferior pedicular components during use, the second attachment element having a proximal end and a distal end, wherein the proximal end has a swivel attachment;
  a first piston partially disposed within and concentric to the receiving portion of the first attachment element, wherein a distal end of the first piston is at least partially contained within the receiving portion of the first attachment element, wherein the first piston is configured to travel longitudinally within the interior of the receiving portion during use, and wherein the portion of the first piston of the first piston at least partially contained within the receiving portion of the first attachment element includes a detent;
  an engagement element configured to engage the second piston during use to inhibit longitudinal movement of the second piston, thereby limiting a longitudinal travel distance of the second piston within the receiving portion;
  a retaining mechanism selectively positionable in one of at least a first position and a second discrete position, wherein the retaining mechanism limits the longitudinal travel of the second piston to a first distance when positioned in the first position and limits the longitudinal travel of the second piston to a second distance greater than the first distance when positioned in the second position; and
  a second piston fully disposed within and concentric to the receiving portion of the first attachment element, the second piston having a diameter less than a diameter of the first piston, wherein the first piston includes a recess at a distal end configured to partially receive the second piston.

28. The strut system of claim 27 wherein the receiving portion is a cylindrical housing having a hollow interior section.

29. The strut system of claim 28, further comprising an internal spring concentric with the housing, the first piston and the second piston, the internal spring having a larger internal diameter than an external diameter of the second piston, and wherein the spring is disposed concentrically about the exterior of the second piston during use such that the spring encircles the second piston.

30. The strut system of claim 29, further comprising a second spring concentric with the housing, the first piston and the second piston, the second spring having a smaller diameter than the diameter of the second piston, and wherein the second spring extends longitudinally from an end of the second piston and is retained in a second recess portion of the first attachment element.

31. The strut system of claim 27, further comprising an engagement element configured to engage the detent of the first piston during use to inhibit longitudinal movement of the piston, thereby limiting a longitudinal travel distance of the first piston within the receiving portion, wherein the retaining mechanism is selectively positionable in one of at least a first discrete position and a second discrete position, wherein the retaining mechanism limits the longitudinal travel of the first piston to a first distance when positioned in the first discrete position and limits the longitudinal travel of the first piston to a second distance greater than the first distance when positioned in the second discrete position.

32. The strut system of claim 27 wherein the engagement element is a set screw.

33. A dynamic stabilizing system configured to be coupled between a first vertebra and a second vertebra of a human spine, the dynamic stabilizing device comprising:
   a first member configured to be coupled to the first vertebra during use, wherein the first member comprises a longitudinal recess;
   a second member configured to be coupled to the second vertebra during use, wherein the second member comprises:
      an elongated protrusion configured to be disposed within the longitudinal recess of the first member during use, wherein the elongated protrusion is configured to travel longitudinally within the longitudinal recess to facilitate movement of the first vertebra relative to the second vertebra during use;
      a detent feature extending radially from the longitudinal protrusion; and
      a spring disposed about a circumference of at least a portion of the elongated protrusion, wherein longitudinal movement of the elongated protrusion within the longitudinal recess is configured to engage the spring to at least partially inhibit movement of the first member relative to the second member; and
   a retaining mechanism configured to engage the detent of the second member to at least partially inhibit longitudinal movement of the elongated protrusion within the longitudinal recess during use, thereby limiting a longitudinal travel distance of the longitudinal protrusion within the longitudinal recess during use, wherein the retaining mechanism is selectively positionable in either one of a first discrete position and a second discrete position, wherein the retaining mechanism limits the longitudinal travel of longitudinal protrusion within the longitudinal recess to a first distance when positioned in the first discrete position and limits the longitudinal travel of longitudinal protrusion within the longitudinal recess to a second distance greater than the first distance when positioned in the second discrete position.

34. The dynamic stabilizing system of claim 33 wherein the second member comprises a wall defining the longitudinal recess, and wherein the retaining mechanism comprises a member extending through a hole in the wall and into an interior of the receiving portion during use, such that at least an end portion of the member engages the detent of the second member to at least partially inhibit longitudinal movement of the elongated protrusion within the longitudinal recess during use.

* * * * *

UNITED STATES PATENT AND TRADEMARK OFFICE
CERTIFICATE OF CORRECTION

PATENT NO. : 8,025,680 B2  Page 1 of 1
APPLICATION NO. : 11/436407
DATED : September 27, 2011
INVENTOR(S) : Hayes et al.

It is certified that error appears in the above-identified patent and that said Letters Patent is hereby corrected as shown below:

In the Claims:

Claim 4, col. 21, line 16, please delete "aset" and substitute therefor -- a set --.

Signed and Sealed this
Tenth Day of January, 2012

David J. Kappos
*Director of the United States Patent and Trademark Office*